(12) United States Patent
Luo et al.

(10) Patent No.: US 10,429,395 B2
(45) Date of Patent: Oct. 1, 2019

(54) GLUCOSE SENSOR SIGNAL STABILITY ANALYSIS

(71) Applicant: Medtronic Minimed, Inc., Northridge, CA (US)

(72) Inventors: Ying Luo, Stevenson Ranch, CA (US); Rebecca K. Gottlieb, Culver City, CA (US); Meena Ramachandran, San Francisco, CA (US); Chia-Hung Chiu, Pasadena, CA (US); Nandita Dangui-Patel, Los Angeles, CA (US); Michael Kremliovsky, Poway, CA (US); Jefferson Rose, Hawthorne, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 84 days.

(21) Appl. No.: 14/796,995

(22) Filed: Jul. 10, 2015

(65) Prior Publication Data
US 2015/0316559 A1   Nov. 5, 2015

Related U.S. Application Data

(63) Continuation of application No. 14/015,937, filed on Aug. 30, 2013, now Pat. No. 9,101,310, which is a
(Continued)

(51) Int. Cl.
*G01N 33/66* (2006.01)
*A61B 5/145* (2006.01)
(Continued)

(52) U.S. Cl.
CPC ........... *G01N 33/66* (2013.01); *A61B 5/1486* (2013.01); *A61B 5/1495* (2013.01);
(Continued)

(58) Field of Classification Search
CPC . A61B 5/14512; A61B 5/1495; A61B 5/6849; A61B 5/1486; A61B 5/0017; A61B 5/002; A61B 5/7207; G01N 33/66
(Continued)

(56) References Cited

U.S. PATENT DOCUMENTS

| 5,028,787 A | 7/1991 | Rosenthal et al. |
| 6,895,263 B2 | 5/2005 | Shin |

(Continued)

FOREIGN PATENT DOCUMENTS

| CN | 1407734 | 2/2003 |
| WO | WO 2006/024671 A1 | 3/2006 |
| WO | WO2008086541 | 11/2008 |

OTHER PUBLICATIONS

Liu et al., "Signal denoising and baseline correction by discrete wavelet transform for microchip capillary electrophoresis," Electrophoresis (2003).*

(Continued)

*Primary Examiner* — Hyun D Park
(74) *Attorney, Agent, or Firm* — Berkeley Law & Technology Group, LLP

(57) ABSTRACT

Disclosed are methods, apparatuses, etc. for glucose sensor signal stability analysis. In certain example embodiments, a series of samples of at least one sensor signal that is responsive to a blood glucose level of a patient may be obtained. Based at least partly on the series of samples, at least one metric may be determined to assess an underlying trend of a change in responsiveness of the at least one sensor signal to the blood glucose level of the patient over time. A reliability of the at least one sensor signal to respond to the blood glucose level of the patient may be assessed based at least partly on the at least one metric assessing the underlying trend. Other example embodiments are disclosed herein.

10 Claims, 20 Drawing Sheets

Related U.S. Application Data continuation of application No. 12/914,969, filed on Oct. 28, 2010, now Pat. No. 8,543,354.

(60) Provisional application No. 61/357,803, filed on Jun. 23, 2010.

(51) Int. Cl.
- A61B 5/1486 (2006.01)
- A61B 5/00 (2006.01)
- A61B 5/1495 (2006.01)

(52) U.S. Cl.
CPC ........ *A61B 5/14532* (2013.01); *A61B 5/6849* (2013.01); *A61B 5/002* (2013.01); *A61B 5/0017* (2013.01); *A61B 5/7207* (2013.01)

(58) Field of Classification Search
USPC .................. 702/179, 182; 600/345, 347, 365
See application file for complete search history.

(56) References Cited

U.S. PATENT DOCUMENTS

| | | | |
|---|---|---|---|
| 7,996,158 B2 | 8/2011 | Hayter et al. | |
| 8,103,471 B2 | 1/2012 | Hayter | |
| 8,239,166 B2 | 8/2012 | Hayter et al. | |
| 8,260,558 B2 | 9/2012 | Hayter et al. | |
| 8,280,523 B2 * | 10/2012 | Keel | A61N 1/36507 607/28 |
| 8,287,453 B2 | 10/2012 | Li et al. | |
| 9,101,310 B2 | 8/2015 | Luo | |
| 2002/0161288 A1 * | 10/2002 | Shin | A61B 5/14532 600/316 |
| 2005/0004439 A1 * | 1/2005 | Shin | A61B 5/14532 600/365 |
| 2006/0016700 A1 * | 1/2006 | Brister | A61B 5/14532 205/777.5 |
| 2008/0000779 A1 * | 1/2008 | Wang | A61B 5/14532 205/775 |
| 2008/0161664 A1 * | 7/2008 | Mastrototaro | A61B 5/14532 600/347 |
| 2008/0221509 A1 | 9/2008 | Gottlieb | |
| 2008/0287761 A1 * | 11/2008 | Hayter | A61B 5/14532 600/365 |
| 2008/0287763 A1 | 11/2008 | Hayter | |
| 2008/0288180 A1 | 11/2008 | Hayter et al. | |
| 2008/0297762 A1 | 12/2008 | Crowe | |
| 2008/0312841 A1 | 12/2008 | Hayter et al. | |
| 2008/0312842 A1 | 12/2008 | Hayter et al. | |
| 2008/0312844 A1 | 12/2008 | Hayter et al. | |
| 2008/0312845 A1 | 12/2008 | Hayter et al. | |
| 2009/0005665 A1 | 1/2009 | Hayter et al. | |
| 2009/0006034 A1 | 1/2009 | Hayter et al. | |
| 2009/0006061 A1 | 1/2009 | Thukral et al. | |
| 2009/0006129 A1 | 1/2009 | Thukral et al. | |
| 2009/0192751 A1 | 7/2009 | Kamath | |
| 2010/0169035 A1 | 7/2010 | Liang | |
| 2011/0004085 A1 | 1/2011 | Mensinger et al. | |
| 2012/0291516 A1 | 11/2012 | Hayter et al. | |

OTHER PUBLICATIONS

Souretis et al., "Blood volume signal analysis with empirical mode decomposition" IEEE 2007.*
Van Den Berghe, Greet, et al., "Intensive Insulin Therapy in Critically Ill Patients" The New England Journal of Medicine, vol. 345, No. 19, Nov. 8, 2001, pp. 1359-1367.
U.S. Appl. No. 12/914,969, filed Oct. 28, 2010, 100 Pages.
U.S. Appl. No. 12/914,969: Notice to File Missing Parts, Filing Receipt, Mailed Nov. 12, 2010, 5 Pages.
U.S. Appl. No. 12/914,969: Applicant Response to pre-Exam Formalities Notice, Mailed Dec. 20, 2010, 9 Pages.
U.S. Appl. No. 12/914,969: Filing Receipt, Mailed Jan. 3, 2011, 3 pages.
U.S. Appl. No. 12/914,969: Documents Submitted with 371 Applications, Mailed Dec. 8, 2011, 14 Pages.
U.S. Appl. No. 12/914,969: Notice of Publication, Mailed Dec. 30, 2011, 1 Page.
U.S. Appl. No. 12/914,969: Non-Final Office Action, Mailed Dec. 10, 2012, 6 Pages.
U.S. Appl. No. 12/914,969: Non-Final Office Action Response, Mailed Apr. 9, 2013, 17 Pages.
U.S. Appl. No. 12/914,969: Notice of Allowance and Fees Due, Mailed May 23, 2013, 15 Pages.
U.S. Appl. No. 12/914,969: Issue Fee Payment (PTO-85B), Mailed Aug. 22, 2013, 5 pages.
U.S. Appl. No. 12/914,969: Issue Notification, Mailed Sep. 4, 2013, 1 Page.
U.S. Appl. No. 14/015,937: Application and Preliminary Amendment as filed Aug. 30, 2013, 97 pages.
U.S. Appl. No. 14/015,937: Filing Receipt mailed Sep. 24, 2013, 3 pages.
U.S. Appl. No. 14/015,937: Notice of Publication mailed Jan. 2, 2014, 1 page.
U.S. Appl. No. 14/015,937: Non-Final Rejection and examiner search, mailed Nov. 28, 2014, 19 pages.
U.S. Appl. No. 14/015,937: Amendment/Req. Reconsideration—After Non-Final Rejection, filed Feb. 24, 2015, 12 pages.
U.S. Appl. No. 14/015,937: Notice of Allowance and Fees due and Examiner search, mailed Apr. 9, 2015, 24 pages.
U.S. Appl. No. 14/015,937: Issue Fee Payment filed Jul. 8, 2015, 1 page.
U.S. Appl. No. 14/015,937: Issue Notification mailed Jul. 22, 2015, 1 page.
PCT/US11/041336: Application as filed on Jun. 22, 2011, 77 pages.
PCT/US11/041336: International Search Report, mailed Nov. 2, 2011, 5 pages.
PCT/US11/041336: Written Opinion, Mailed Nov. 2, 2011, 7 Pages.
PCT/US11/041336: International Preliminary Report on Patentability, Mailed Jul. 22, 2011, 8 Pages.
PCT/US11/041336: Initial Publication with ISR, Mailed Nov. 2, 2011, 73 Pages.
11738681.1: Response to EPO Office Action, mailed Jan. 23, 2015, 2 pages.
Examiner's Report, dated 1 Mar. 17, 2017, CA App No. 2800833 / (PCT US2011041336).
EP App No. 11738861.1 / Communication pursuant to Article 94(3) EPC, mailed Aug. 1, 2016, 4 pages.
EP App No. 11738861.1 / Reply to communication from the Examining Division, filed Jan. 5, 2017, 2 pages.
EP App 11738861.1: Communication pursuant to Article 94(3) EPC, dated May 18, 2017, 3 pages.
EPA 11738681.1: Response and Amended claims, dated Nov. 16, 2017, 10 pages.
JP 2016066263: Decision of Rejection, dated Oct. 31, 2017, 4 pages.
CN 201510882048.4: Office Action, dated Aug. 18, 2017, 12 pages.
CA 2800833: Examiner's Report, dated Nov. 6, 2017, 4 pages.
CA 2800833: Amendment/Remarks After Examiner's Report, dated May 7, 2018, 15 pages.
EPO 11 738 861.1: Office Action, dated Oct. 4, 2018, 5 pages.
CA 2800833: Notice of Allowance, dated Sep. 4, 2018, 1 page.
CA 2800833: Section 8 Correction, dated Oct. 26, 2018, 3 pages.
EPA 11738681.1: Response to Office Action, dated Mar. 14, 2019, 10 pages.

* cited by examiner

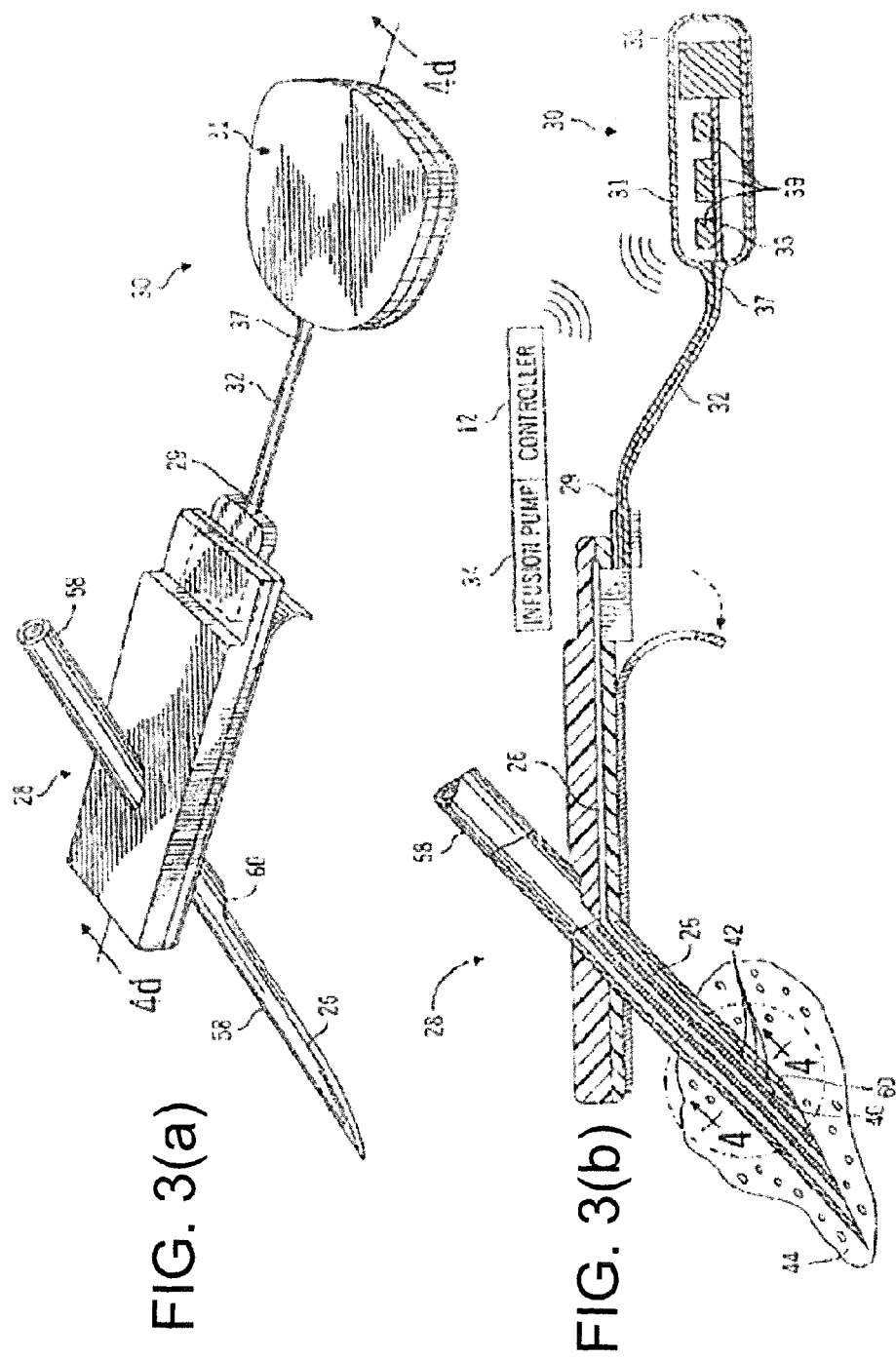

GLUCOSE SENSOR SIGNAL STABILITY ANALYSIS

CROSS-REFERENCE TO RELATED APPLICATION(S)

This U.S. Non-Provisional patent application claims the benefit of co-pending U.S. Non-Provisional patent application Ser. No. 14/015,937, filed on 30 Aug. 2013, entitled "GLUCOSE SENSOR STABILITY ANALYSIS"; U.S. Non-Provisional patent application Ser. No. 12/914,969, filed on 28 Oct. 2010, issued as U.S. Pat. No. 8,543,354 on 4 Sep. 2013, entitled "GLUCOSE SENSOR SIGNAL STABILITY ANALYSIS"; and U.S. Provisional Patent Application No. 61/357,803, filed 23 Jun. 2010, entitled "SENSOR SYSTEMS HAVING MULTIPLE PROBES AND ELECTRODE ARRAYS," and which are all hereby incorporated by reference herein.

BACKGROUND

1. Field

Subject matter disclosed herein relates to glucose sensor signal stability analysis including, by way of example but not limitation, analyzing a reliability of a glucose sensor signal by attempting to detect a change in responsiveness of the sensor signal.

2. Information

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, which is a condition known as Type I diabetes mellitus (or in some cases, if β-cells produce insufficient quantities of insulin, a condition known as Type II diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of the Type I diabetic individuals in the United States were using infusion pump therapy. Over time, greater than 7% of the more than 900,000 Type I diabetic individuals in the U.S. began using infusion pump therapy. The percentage of Type I diabetic individuals that use an infusion pump is now growing at a rate of over 2% each year. Moreover, the number of Type II diabetic individuals is growing at 3% or more per year, and increasing numbers of insulin-using Type II diabetic individuals are also adopting infusion pumps. Physicians have recognized that continuous infusion can provide greater control of a diabetic individual's condition, so they are increasingly prescribing it for patients.

A closed-loop infusion pump system may include an infusion pump that is automatically and/or semi-automatically controlled to infuse insulin into a patient. The infusion of insulin may be controlled to occur at times and/or in amounts that are based, for example, on blood glucose measurements obtained from an embedded blood-glucose sensor, e.g., in real-time. Closed-loop infusion pump systems may also employ the delivery of glucagon, in addition to the delivery of insulin, for controlling blood-glucose and/or insulin levels of a patient (e.g., in a hypoglycemic context). Glucagon delivery may also be based, for example, on blood glucose measurements that are obtained from an embedded blood-glucose sensor, e.g., in real-time.

SUMMARY

Briefly, example embodiments may relate to methods, systems, apparatuses, and/or articles, etc. for glucose sensor signal reliability analysis. Glucose monitoring systems, including ones that are designed to adjust the glucose levels of a patient and/or to operate continually (e.g., repeatedly, at regular intervals, at least substantially continuously, etc.), may comprise a glucose sensor signal that may be assessed for reliability. More specifically, but by way of example only, reliability assessment(s) on glucose sensor signals may include glucose sensor signal stability assessment(s) to detect an apparent change in responsiveness of a signal.

In one or more example embodiments, a method may include: obtaining a series of samples of at least one sensor signal that is responsive to a blood glucose level of a patient; determining, based at least partly on the series of samples, at least one metric assessing an underlying trend of a change in responsiveness of the at least one sensor signal to the blood glucose level of the patient over time; and assessing a reliability of the at least one sensor signal to respond to the blood glucose level of the patient based at least partly on the at least one metric assessing an underlying trend.

In at least one example implementation, the method may further include: generating an alert signal responsive to a comparison of the at least one metric assessing an underlying trend with at least one predetermined threshold.

In at least one example implementation, the assessing may include: comparing the at least one metric assessing an underlying trend with at least a first predetermined threshold and a second predetermined threshold. In at least one other example implementation, the assessing may further include: assessing that the reliability of the at least one sensor signal is in a first state responsive to a comparison of the at least one metric assessing an underlying trend with the first predetermined threshold; assessing that the reliability of the at least one sensor signal is in a second state responsive to a comparison of the at least one metric assessing an underlying trend with the first predetermined threshold and the second predetermined threshold; and assessing that the reliability of the at least one sensor signal is in a third state responsive to a comparison of the at least one metric assessing an underlying trend with the second predetermined threshold. In at least one other example implementation, the assessing may further include: ascertaining at least one value indicating a severity of divergence by the at least one sensor signal from the blood glucose level of the patient over time based at least partly on the at least one metric assessing an underlying trend, the first predetermined threshold, and the second predetermined threshold.

In at least one example implementation, the method may further include: acquiring the at least one sensor signal from one or more subcutaneous glucose sensors, wherein the at least one metric assessing an underlying trend may reflect an apparent reliability of the at least one sensor signal that is acquired from the one or more subcutaneous glucose sensors. In at least one example implementation, the method may further include: altering an insulin infusion treatment for the patient responsive at least partly to the assessed reliability of the at least one sensor signal.

In at least one example implementation, the determining may include: producing the at least one metric assessing an underlying trend using a slope of a linear regression that is derived at least partly from the series of samples of the at least one sensor signal. In at least one other example implementation, the method may include: transforming the series of samples of the at least one sensor signal to derive a monotonic curve, wherein the producing may include calculating the slope of the linear regression, with the linear regression being derived at least partly from the monotonic curve.

In at least one example implementation, the determining may include: decomposing the at least one sensor signal as represented by the series of samples using at least one empirical mode decomposition and one or more spline functions to remove relatively higher frequency components from the at least one sensor signal. In at least one example implementation, the determining may include: decomposing the at least one sensor signal as represented by the series of samples using at least one discrete wavelet transform; and reconstructing a smoothed signal from one or more approximation coefficients resulting from the at least one discrete wavelet transform. In at least one example implementation, the determining may include: iteratively updating a trend estimation at multiple samples of the series of samples of the at least one sensor signal based at least partly on a trend estimation at a previous sample and a growth term.

In one or more example embodiments, an apparatus may include: a controller to obtain a series of samples of at least one sensor signal that is responsive to a blood glucose level of a patient, and the controller may include one or more processors to: determine, based at least partly on the series of samples, at least one metric assessing an underlying trend of a change in responsiveness of the at least one sensor signal to the blood glucose level of the patient over time; and assess a reliability of the at least one sensor signal to respond to the blood glucose level of the patient based at least partly on the at least one metric assessing an underlying trend.

In at least one example implementation, the one or more processors of the controller may further be to: generate an alert signal responsive to a comparison of the at least one metric assessing an underlying trend with at least one predetermined threshold.

In at least one example implementation, the controller may be capable of assessing by: comparing the at least one metric assessing an underlying trend with at least a first predetermined threshold and a second predetermined threshold. In at least one other example implementation, the controller may be further capable of assessing by: assessing that the reliability of the at least one sensor signal is in a first state responsive to a comparison of the at least one metric assessing an underlying trend with the first predetermined threshold; assessing that the reliability of the at least one sensor signal is in a second state responsive to a comparison of the at least one metric assessing an underlying trend with the first predetermined threshold and the second predetermined threshold; and assessing that the reliability of the at least one sensor signal is in a third state responsive to a comparison of the at least one metric assessing an underlying trend with the second predetermined threshold. In at least one other example implementation, the controller may be further capable of assessing by: ascertaining at least one value indicating a severity of divergence by the at least one sensor signal from the blood glucose level of the patient over time based at least partly on the at least one metric assessing an underlying trend, the first predetermined threshold, and the second predetermined threshold.

In at least one example implementation, the one or more processors of the controller may further be to: acquire the at least one sensor signal from one or more subcutaneous glucose sensors, wherein the at least one metric assessing an underlying trend may reflect an apparent reliability of the at least one sensor signal that is acquired from the one or more subcutaneous glucose sensors. In at least one example implementation, the one or more processors of the controller may further be to: alter an insulin infusion treatment for the patient responsive at least partly to the assessed reliability of the at least one sensor signal.

In at least one example implementation, the controller may be capable of determining by: producing the at least one metric assessing an underlying trend using a slope of a linear regression that is derived at least partly from the series of samples of the at least one sensor signal. In at least one example implementation, the one or more processors of the controller may further be to: transform the series of samples of the at least one sensor signal to derive a monotonic curve, wherein the controller may be capable of producing the at least one metric assessing an underlying trend by calculating the slope of the linear regression, with the linear regression being derived at least partly from the monotonic curve.

In at least one example implementation, the controller may be capable of determining by: decomposing the at least one sensor signal as represented by the series of samples using at least one empirical mode decomposition and one or more spline functions to remove relatively higher frequency components from the at least one sensor signal. In at least one example implementation, the controller may be capable of determining by: decomposing the at least one sensor signal as represented by the series of samples using at least one discrete wavelet transform; and reconstructing a smoothed signal from one or more approximation coefficients resulting from the at least one discrete wavelet transform. In at least one example implementation, the controller may be capable of determining by: iteratively updating a trend estimation at multiple samples of the series of samples of the at least one sensor signal based at least partly on a trend estimation at a previous sample and a growth term.

In one or more example embodiments, a system may include: means for obtaining a series of samples of at least one sensor signal that is responsive to a blood glucose level of a patient; means for determining, based at least partly on the series of samples, at least one metric assessing an underlying trend of a change in responsiveness of the at least one sensor signal to the blood glucose level of the patient over time; and means for assessing a reliability of the at least one sensor signal to respond to the blood glucose level of the patient based at least partly on the at least one metric assessing an underlying trend.

In one or more example embodiments, an article may include at least one storage medium having stored thereon instructions executable by one or more processors to: obtain a series of samples of at least one sensor signal that is responsive to a blood glucose level of a patient; determine, based at least partly on the series of samples, at least one metric assessing an underlying trend of a change in responsiveness of the at least one sensor signal to the blood glucose level of the patient over time; and assess a reliability of the at least one sensor signal to respond to the blood glucose level of the patient based at least partly on the at least one metric assessing an underlying trend.

Other alternative example embodiments are described herein and/or illustrated in the accompanying Drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular example embodiments, a sensor may be adapted to generate one or more signals responsive to a measured blood glucose concentration in a body while a special purpose computing device and/or processor may be adapted to perform at least a portion of described method(s) according to one or more particular implementations based upon the one or more signals generated by the sensor.

BRIEF DESCRIPTION OF THE FIGURES

Non-limiting and non-exhaustive features are described with reference to the following figures, wherein like reference numerals refer to like and/or analogous parts throughout the various figures:

FIG. 3(a) is a perspective view of an example glucose sensor system for use in accordance with an embodiment.

FIG. 3(b) is a side cross-sectional view of a glucose sensor system of FIG. 3(a) for an embodiment.

DETAILED DESCRIPTION

Figure 1:
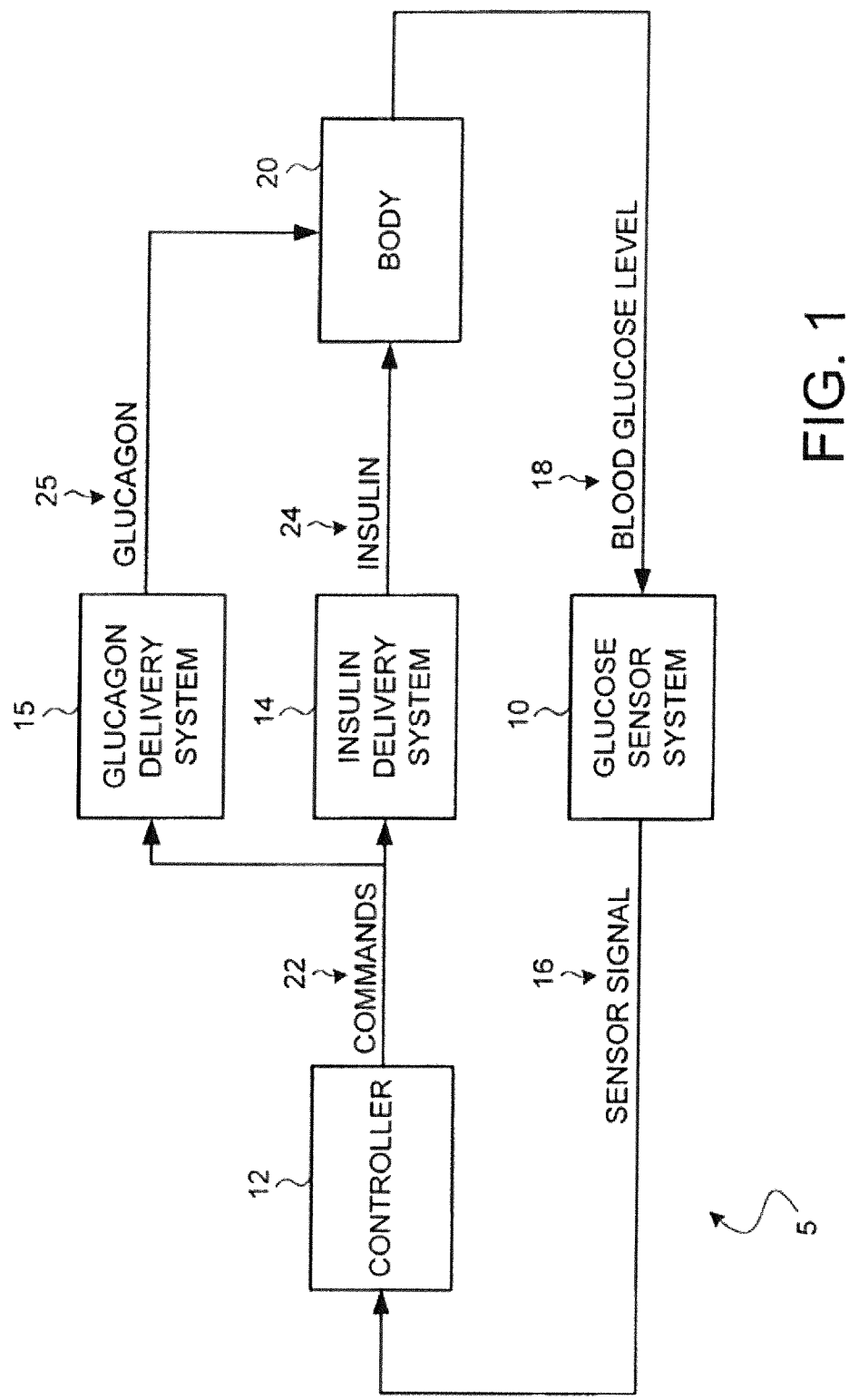
FIG. 1 is a schematic diagram of an example closed loop glucose control system in accordance with an embodiment.

In an example glucose monitoring sensor and/or insulin delivery system environment, measurements reflecting blood-glucose levels may be employed in a closed loop infusion system for regulating a rate of fluid infusion into a body. In particular example embodiments, a sensor and/or system may be adapted to regulate a rate of insulin and/or glucagon infusion into a body of a patient based, at least in part, on a glucose concentration measurement taken from a body (e.g., from a blood-glucose sensor, including a current sensor). In certain example implementations, such a system may be designed to model a pancreatic beta cell (β-cell). Here, such a system may control an infusion device to release insulin into a body of a patient in an at least approximately similar concentration profile as might be created by fully functioning human β-cells, if such were responding to changes in blood glucose concentrations in the body. Thus, such a closed loop infusion system may simulate a body's natural insulin response to blood glucose levels. Moreover, it may not only make efficient use of insulin, but it may also account for other bodily functions as well because insulin can have both metabolic and mitogenic effects.

According to certain embodiments, examples of closed-loop systems as described herein may be implemented in a hospital environment to monitor and/or control levels of glucose and/or insulin in a patient. Here, as part of a hospital or other medical facility procedure, a caretaker or attendant may be tasked with interacting with a closed-loop system to, for example: enter blood-glucose reference measurement samples into control equipment to calibrate blood glucose measurements obtained from blood-glucose sensors, make manual adjustments to devices, and/or make changes to therapies, just to name a few examples. Alternatively, according to certain embodiments, examples of closed-loop systems as described herein may be implemented in non-hospital environments to monitor and/or control levels of glucose and/or insulin in a patient. Here, a patient or other non-medical professional may be involved in interacting with a closed-loop system.

However, while a closed-loop glucose control system is active, oversight by medical professionals, patients, non-medical professionals, etc. is typically reduced. Such a closed-loop glucose control system may become at least partially responsible for the health, and possibly the survival, of a diabetic patient. To more accurately control blood glucose levels of a patient, a closed-loop system may be provided knowledge of a current blood glucose level. One approach to providing such knowledge is implementation of a blood glucose sensor, such as including one or more such glucose sensors in a closed-loop system.

A closed-loop system may receive at least one glucose sensor signal from one or more glucose sensors, with the glucose sensor signal intended to accurately represent a current (or at least relatively current) blood glucose level. If a glucose sensor signal indicates that a blood glucose level is currently too high, then a closed-loop system may take action(s) to lower it. On the other hand, if a glucose sensor signal indicates that a blood glucose level is currently too low, then a closed-loop system may take action(s) to raise it. Actions taken by a closed-loop system to control blood glucose levels of a patient and protect the patient's health may therefore be based at least partly on a glucose sensor signal received from a glucose sensor.

Unfortunately, a received glucose sensor signal may not be completely reliable as a representation of a current blood glucose level of a patient. For example, a received signal may include impurities that obscure a blood glucose level that actually exists in a body currently. By way of example but not limitation, impurities may be introduced if a sensor measures an incorrect blood glucose level (e.g., due to localized pressure at a sensor site, due to improper sensor hydration, due to inflammatory response, etc.), if noise or other factors impact a blood glucose level signal after measurement, combinations thereof, and so forth. Alternatively and/or additionally, a glucose sensor may gradually become increasingly less stable in its responsiveness, such as by becoming increasingly less capable of accurately measuring a current blood glucose level. In such situations (and/or other ones), a glucose sensor signal that is received at a controller of a closed-loop system may not be sufficiently reliable to justify entrusting a patient's life and health to its control decisions.

In certain embodiments that are described herein, a closed loop system may assess a reliability of at least one sensor signal with respect to its ability to accurately reflect a blood glucose level of a patient based at least partly on at least one metric. In an example embodiment, a metric may characterize one or more non-physiological anomalies of a representation of a blood glucose level of a patient by at least one sensor signal. In another example embodiment, a metric may assess an underlying trend of a change in responsiveness of at least one sensor signal to a blood glucose level of a patient over time. These and other example implementations are described further herein below.

FIG. 1 is a block diagram of an example closed loop glucose control system 5 in accordance with an embodiment. Particular embodiments may include a glucose sensor system 10, a controller 12, an insulin delivery system 14, and a glucagon delivery system 15, etc. as shown in FIG. 1.

In certain example embodiments, glucose sensor system 10 may generate a sensor signal 16 representative of blood glucose levels 18 in body 20, and glucose sensor system 10 may provide sensor signal 16 to controller 12. Controller 12 may receive sensor signal 16 and generate commands 22 that are communicated at least to insulin delivery system 14 and/or glucagon delivery system 15. Insulin delivery system 14 may receive commands 22 and infuse insulin 24 into body 20 in response to commands 22. Likewise, glucagon delivery system 15 may receive commands 22 from controller 12 and infuse glucagon 25 into body 20 in response to commands 22.

Glucose sensor system 10 may include, by way of example but not limitation, a glucose sensor; sensor electrical components to provide power to a glucose sensor and to generate sensor signal 16; a sensor communication system to carry sensor signal 16 to controller 12; a sensor system housing for holding, covering, and/or containing electrical components and a sensor communication system; any combination thereof, and so forth.

Figure 9:
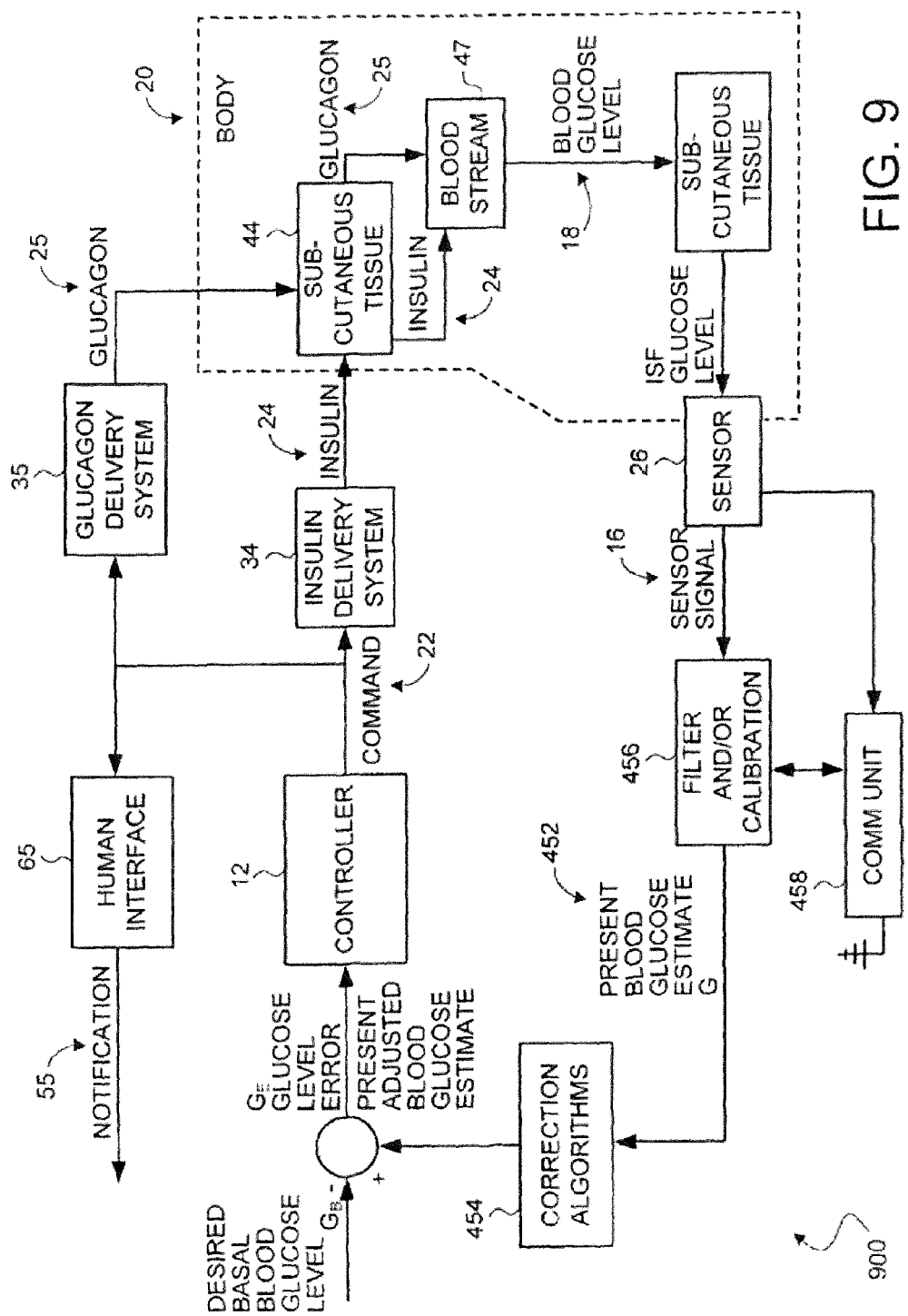
FIG. 9 is a schematic diagram of an example closed loop system to control blood glucose levels via insulin infusion and/or glucagon infusion using at least a controller based on glucose level feedback via a sensor signal in accordance with an embodiment.

Controller 12 may include, by way of example but not limitation, electrical components, other hardware, firmware, and/or software, etc. to generate commands 22 for insulin delivery system 14 and/or glucagon delivery system 15 based at least partly on sensor signal 16. Controller 12 may also include a controller communication system to receive sensor signal 16 and/or to provide commands 22 to insulin delivery system 14 and/or glucagon delivery system 15. In particular example implementations, controller 12 may include a user interface and/or operator interface (e.g., a human interface as shown in FIG. 9) comprising a data input device and/or a data output device. Such a data output device may, for example, generate signals to initiate an alarm and/or include a display or printer for showing a status of controller 12 and/or a patient's vital indicators, monitored historical data, combinations thereof, and so forth. Such a data input device may comprise dials, buttons, pointing devices, manual switches, alphanumeric keys, a touch-sensitive display, combinations thereof, and/or the like for receiving user and/or operator inputs. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 15 may include an infusion device and/or an infusion tube to infuse glucagon 25 into body 20. In alternative embodiments, insulin 24 and glucagon 25 may be infused into body 20 using a shared infusion tube. In other alternative embodiments, insulin 24 and/or glucagon 25 may be infused using an intravenous system for providing fluids to a patient (e.g., in a hospital or other medical environment). When an intravenous system is employed, glucose may be infused directly into a bloodstream of a body instead of or in addition to infusing glucagon into interstitial tissue. It should also be understood that certain example embodiments for closed loop glucose control system 5 may include an insulin delivery system 14 without a glucagon delivery system 15 (or vice versa).

In particular example embodiments, an infusion device (not explicitly identified in FIG. 1) may include infusion electrical components to activate an infusion motor according to commands 22; an infusion communication system to receive commands 22 from controller 12; an infusion device housing (not shown) to hold, cover, and/or contain the infusion device; any combination thereof; and so forth.

In particular example embodiments, controller 12 may be housed in an infusion device housing, and an infusion communication system may comprise an electrical trace or a wire that carries commands 22 from controller 12 to an infusion device. In alternative embodiments, controller 12 may be housed in a sensor system housing, and a sensor communication system may comprise an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within one shared housing. In further alternative embodiments, a sensor, a controller, and/or infusion communication systems may utilize a cable; a wire; a fiber optic line; RF, IR, or ultrasonic transmitters and receivers; combinations thereof; and/or the like instead of electrical traces, just to name a few examples.

Overview of Example Systems

Figure 2:
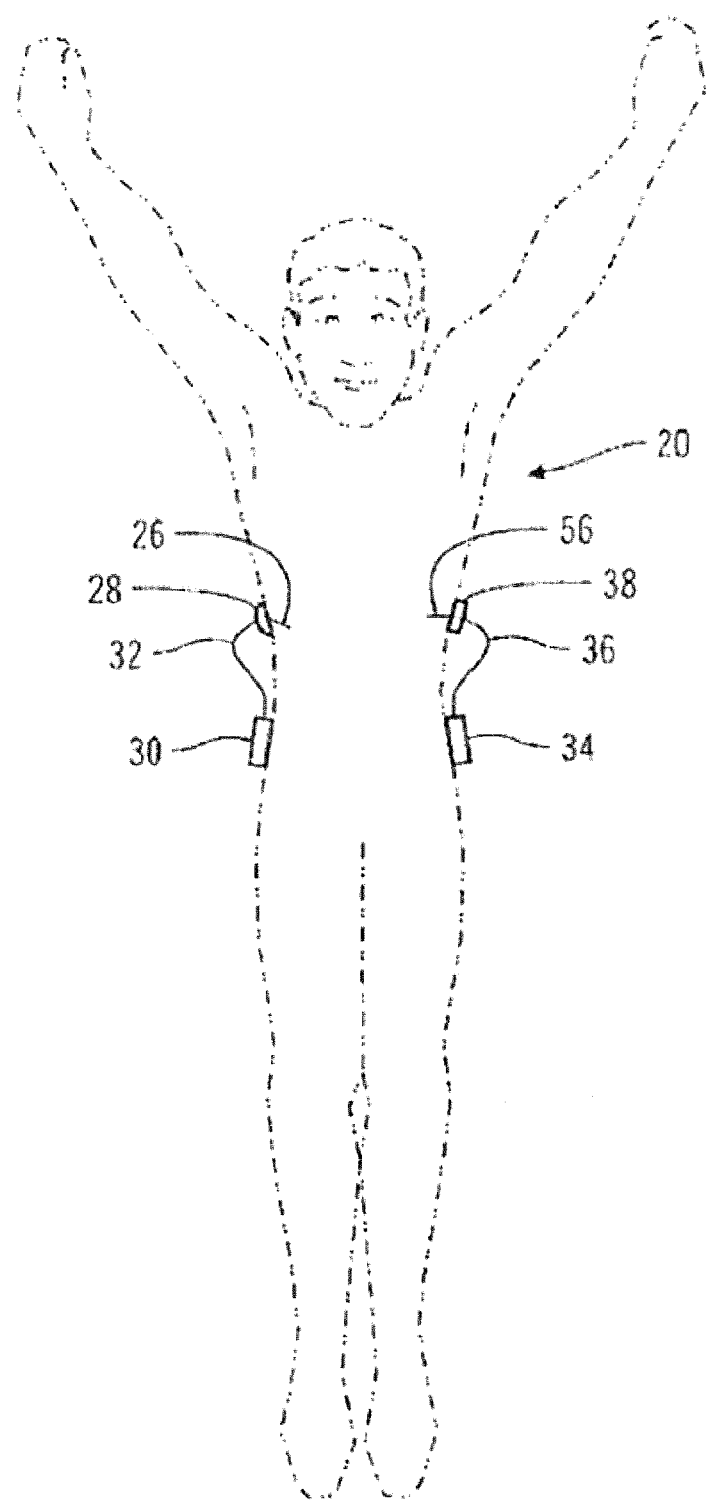
FIG. 2 is a front view of example closed loop hardware located on a body in accordance with an embodiment.
Figure 3C:
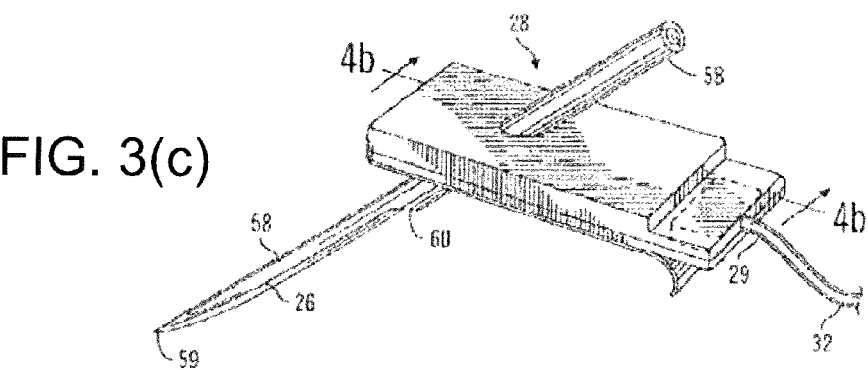
FIG. 3(c) is a perspective view of an example sensor set for a glucose sensor system of FIG. 3(a) for use in accordance with an embodiment.
Figure 3D:
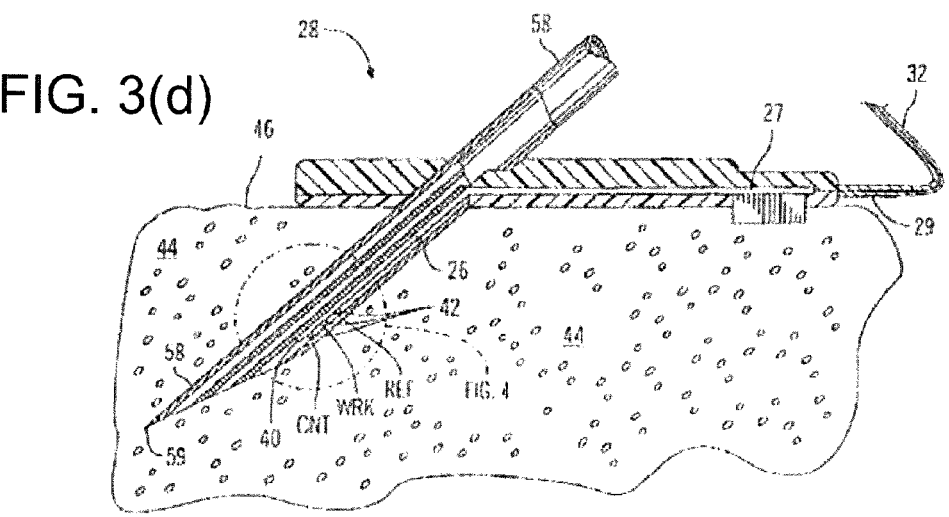
FIG. 3(d) is a side cross-sectional view of a sensor set of FIG. 3(c) for an embodiment.
Figure 4:
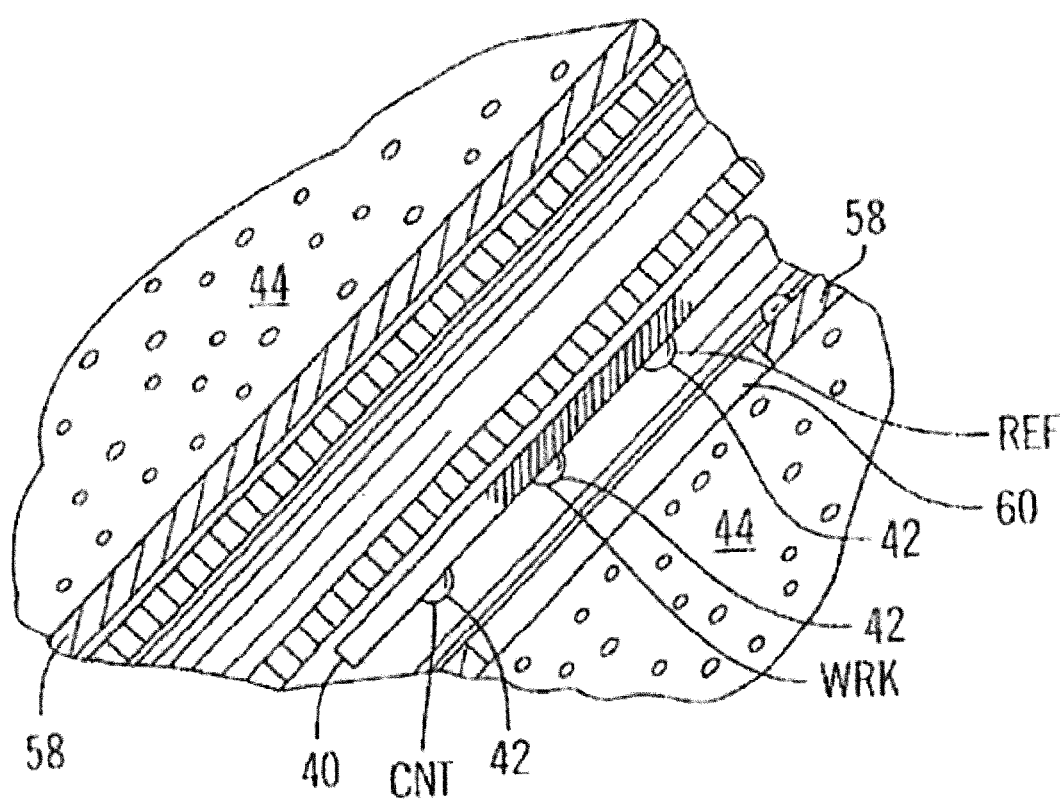
FIG. 4 is a cross sectional view of an example sensing end of a sensor set of FIG. 3(d) for use in accordance with an embodiment.
Figure 5:
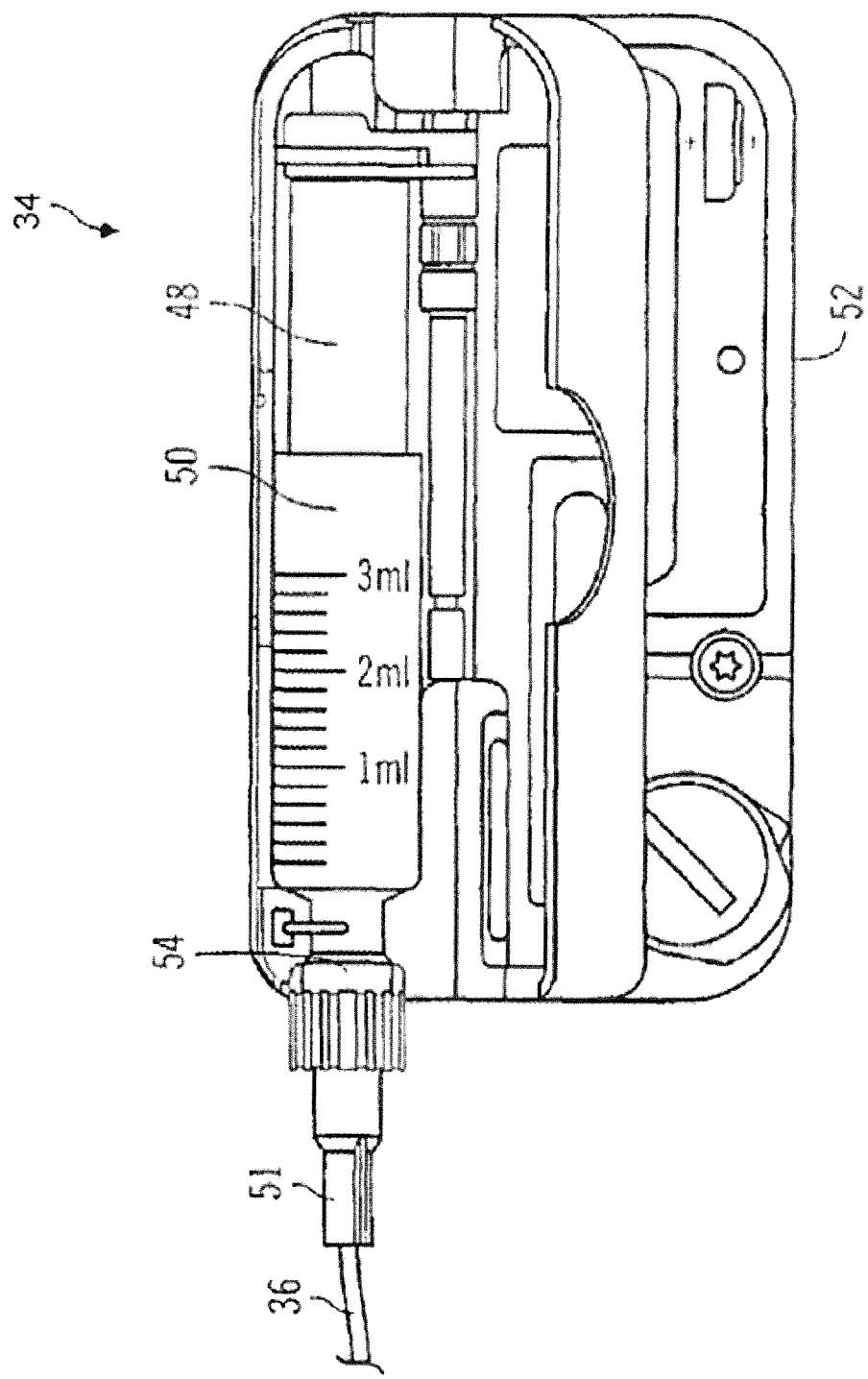
FIG. 5 is a top view of an example infusion device with a reservoir door in an open position, for use according to an embodiment.
Figure 6:
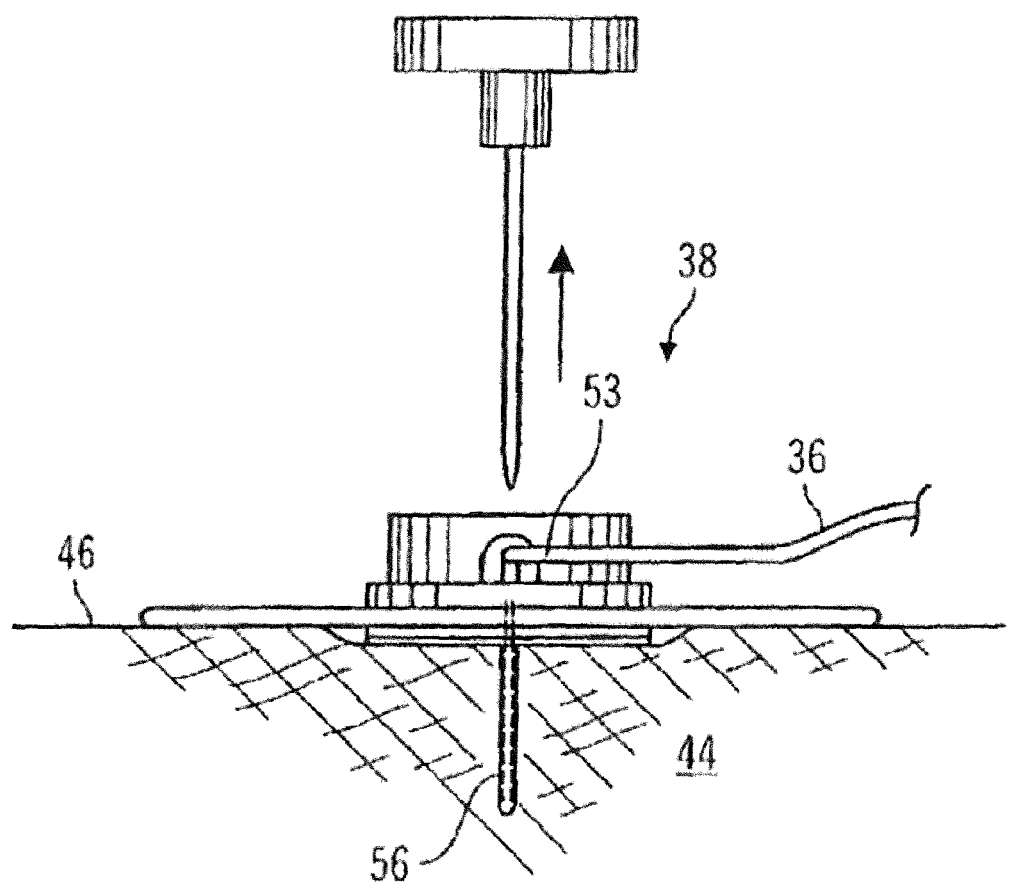
FIG. 6 is a side view of an example infusion set with an insertion needle pulled out, for use according to an embodiment.

FIGS. 2-6 illustrate example glucose control systems in accordance with certain embodiments. FIG. 2 is a front view of example closed loop hardware located on a body in accordance with certain embodiments. FIGS. 3(a)-3(d) and 4 show different views and portions of an example glucose sensor system for use in accordance with certain embodiments. FIG. 5 is a top view of an example infusion device with a reservoir door in an open position in accordance with certain embodiments. FIG. 6 is a side view of an example infusion set with an insertion needle pulled out in accordance with certain embodiments.

Particular example embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. As shown in FIGS. 3(a) and 3(b), telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 3(d) and 4. Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 3(c) and 3(d). Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 2 and 5 (and FIG. 1), a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucose may be infused from a reservoir responsive to commands 22 using a similar and/or analogous device (not shown). In alternative implementations, glucose may be administered to a patient orally.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 2 and 6). With reference to FIG. 6 (and FIG. 1), insulin 24 (e.g., of FIG. 1) may be forced through infusion tube 36 into infusion set 38 and into body 16 (e.g., of FIG. 1). Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 5) and subcutaneous tissue 44 of a user's body 16.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular example implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, anticoagulants, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 26, sensor set 28, telemetered characteristic monitor 30, sensor cable 32, infusion tube 36, infusion set 38, and so forth. Instead, standard blood glucose meters and/or vascular glucose sensors, such as those described in co-pending U.S. Patent Application Publication No. 2008/0221509 (U.S. patent application Ser. No. 12/121,647; to Gottlieb, Rebecca et al.; entitled "MULTILUMEN CATHETER"), filed 15 May 2008, may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

Example System and/or Environmental Delays

Example system and/or environmental delays are described herein. Ideally, a sensor and associated component(s) would be capable of providing a real time, noise-free measurement of a parameter, such as a blood glucose measurement, that a control system is intended to control. However, in real-world implementations, there are typically physiological, chemical, electrical, algorithmic, and/or other sources of time delays that cause a sensor measurement to lag behind an actual present value. Also, as noted herein, such a delay may arise from, for instance, a particular level of noise filtering that is applied to a sensor signal.

Figure 7:
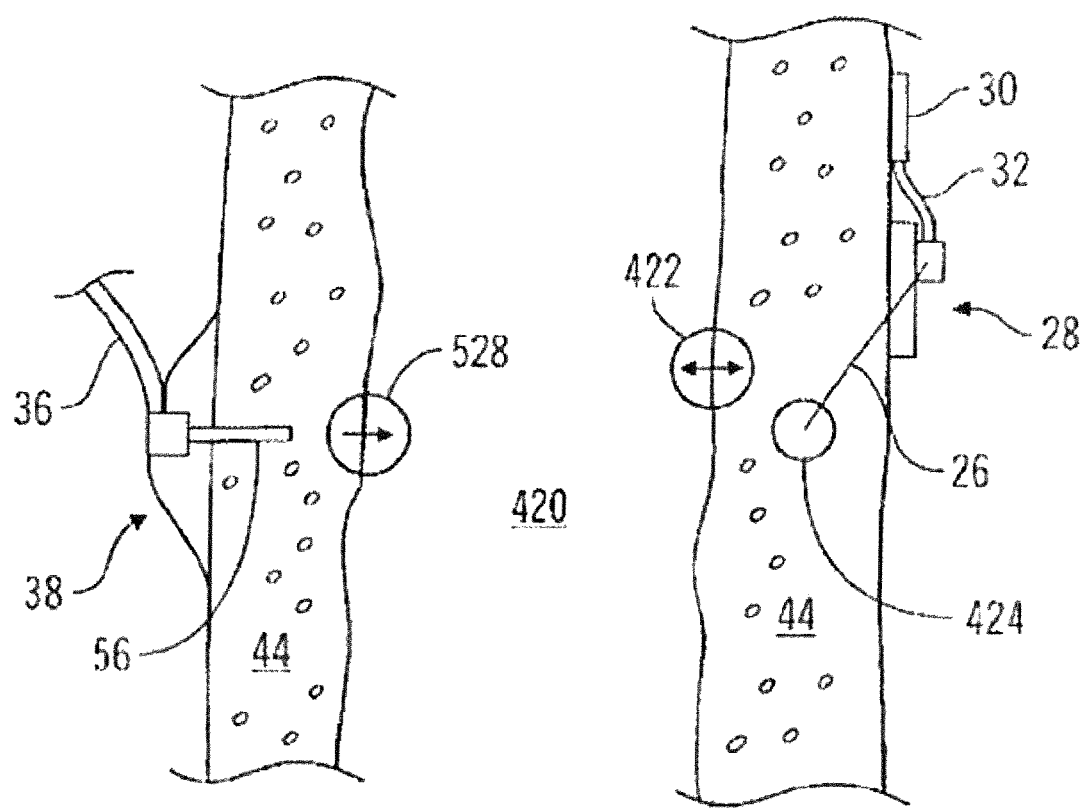
FIG. 7 is a cross-sectional view of an example sensor set and an example infusion set attached to a body in accordance with an embodiment.

FIG. 7 is a cross-sectional view of an example sensor set and an example infusion set that is attached to a body in accordance with an embodiment. In particular example implementations, as shown in FIG. 7, a physiological delay may arise from a time that transpires while glucose moves between blood plasma 420 and interstitial fluid (ISF). This example delay may be represented by a circled double-headed arrow 422. As discussed above with reference to FIG. 2-6, a sensor may be inserted into subcutaneous tissue 44 of body 20 such that electrode(s) 42 (e.g., of FIGS. 3(a)-3(d) and 4) near a tip, or sending end 40, of sensor 26 are in contact with ISF. However, a parameter to be measured may include a concentration of glucose in blood.

Glucose may be carried throughout a body in blood plasma 420. Through a process of diffusion, glucose may move from blood plasma 420 into ISF of subcutaneous tissue 44 and vice versa. As blood glucose level 18 (e.g., of FIG. 1) changes, so does a glucose level of ISF. However, a glucose level of ISF may lag behind blood glucose level 18 due to a time required for a body to achieve glucose concentration equilibrium between blood plasma 420 and ISF. Some studies have shown that glucose lag times between blood plasma and ISF may vary between, e.g., 0 to 30 minutes. Some parameters that may affect such a glucose lag time between blood plasma and ISF are an individual's metabolism, a current blood glucose level, whether a glucose level is rising or falling, combinations thereof, and so forth, just to name a few examples.

A chemical reaction delay 424 may be introduced by sensor response times, as represented by a circle 424 that surrounds a tip of sensor 26 in FIG. 7. Sensor electrodes 42 (e.g., of FIGS. 3(a)-3(d) and 4) may be coated with protective membranes that keep electrodes 42 wetted with ISF, attenuate the glucose concentration, and reduce glucose concentration fluctuations on an electrode surface. As glucose levels change, such protective membranes may slow the rate of glucose exchange between ISF and an electrode surface. In addition, there may be chemical reaction delay(s) due to a reaction time for glucose to react with glucose oxidase GOX to generate hydrogen peroxide and a reaction time for a secondary reaction, such as a reduction of hydrogen peroxide to water, oxygen, and free electrons.

Thus, an insulin delivery delay may be caused by a diffusion delay, which may be a time for insulin that has been infused into a tissue to diffuse into the blood stream. Other contributors to insulin delivery delay may include, but are not limited to: a time for a delivery system to deliver insulin to a body after receiving a command to infuse insulin; a time for insulin to spread throughout a circulatory system once it has entered the blood stream; and/or by other mechanical, electrical/electronic, or physiological causes alone or in combination, just to name a few examples. In addition, a body clears insulin even while an insulin dose is being delivered from an insulin delivery system into the body. Because insulin is continuously cleared from blood plasma by a body, an insulin dose that is delivered to blood plasma too slowly or is delayed is at least partially, and possibly significantly, cleared before the entire insulin dose fully reaches blood plasma. Therefore, an insulin concentration profile in blood plasma may never achieve a given peak (nor follow a given profile) that it may have achieved if there were no delay.

Moreover, there may also be a processing delay as an analog sensor signal Isig is converted to digital sensor values Dsig. In particular example embodiments, an analog sensor signal Isig may be integrated over one-minute intervals and converted to a number of counts. Thus, in such a case, an analog-to-digital (A/D) conversion time may result in an average delay of 30 seconds. In particular example embodiments, one-minute values may be averaged into 5-minute values before they are provided to controller 12 (e.g., of FIG. 1). A resulting average delay may be two-and-one-half minutes (e.g., half of the averaging interval). In example alternative embodiments, longer or shorter integration times may be used that result in longer or shorter delay times.

In other example embodiments, an analog sensor signal current Isig may be continuously converted to an analog voltage Vsig, and an A/D converter may sample voltage Vsig every 10 seconds. Thus, in such a case, six 10-second values may be pre-filtered and averaged to create a one-minute value. Also, five one-minute values may be filtered and averaged to create a five-minute value that results in an average delay of two-and-one-half minutes. In other alternative embodiments, other sensor signals from other types of sensors may be converted to digital sensor values Dsig as appropriate before transmitting the digital sensor values Dsig to another device. Moreover, other embodiments may use other electrical components, other sampling rates, other conversions, other delay periods, a combination thereof, and so forth.

System Configuration Examples

FIGS. 8(a)-8(d) illustrate example diagrams of one or more devices and their components for glucose control systems in accordance with certain embodiments. These FIGS. 8(a)-8(d) show exemplary, but not limiting, illustrations of components that may be utilized with certain controller(s) that are described herein above. Various changes in components, layouts of such components, combinations of elements, and so forth may be made without departing from the scope of claimed subject matter.

Figure 8A:
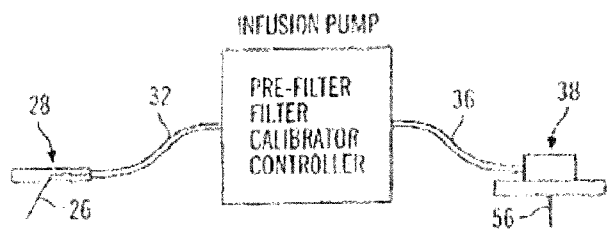
FIG. 8(a) is a diagram of an example single device and its components for a glucose control system in accordance with an embodiment.

Before it is provided as an input to controller 12 (e.g., of FIG. 1), a sensor signal 16 may be subjected to signal conditioning such as pre-filtering, filtering, calibrating, and so forth, just to name a few examples. Components such as a pre-filter, one or more filters, a calibrator, controller 12, etc. may be separately partitioned or physically located together (e.g., as shown in FIG. 8(a)), and they may be included with a telemetered characteristic monitor transmitter 30, an infusion device 34, a supplemental device, and so forth.

Figure 8B:
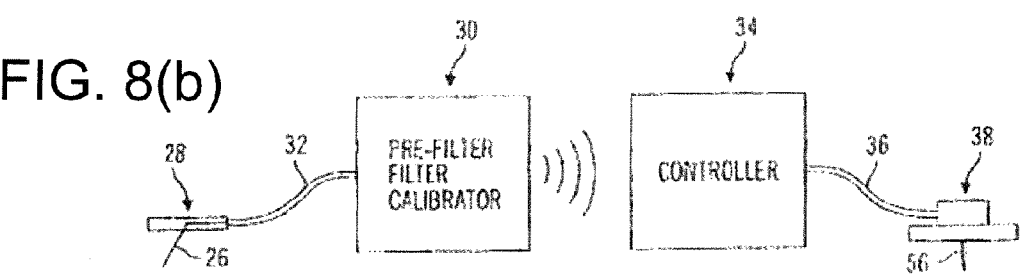
FIG. 8(b) is a diagram of two example devices and their components for a glucose control system in accordance with an embodiment.
Figure 8C:
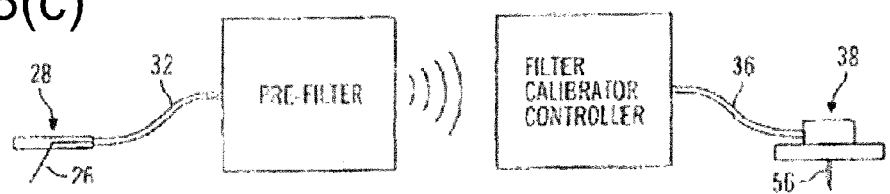
FIG. 8(c) is another diagram of two example devices and their components for a glucose control system in accordance with an embodiment.
Figure 8D:
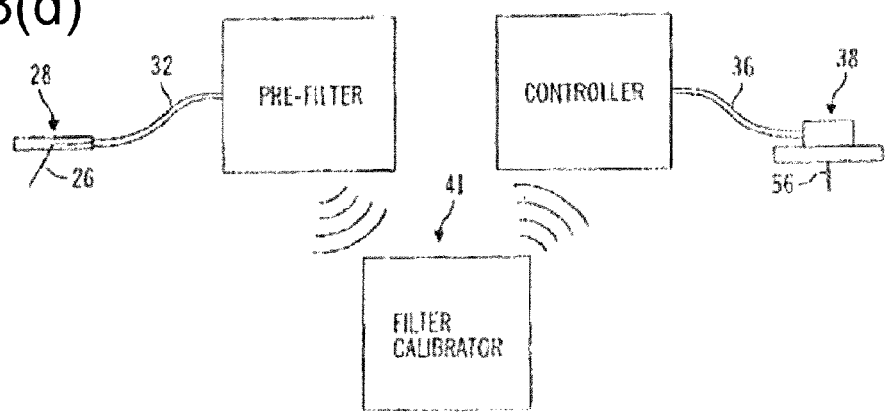
FIG. 8(d) is a diagram of three example devices and their components for a glucose control system in accordance with an embodiment.

In particular example embodiments, a pre-filter, filter(s), and a calibrator may be included as part of telemetered characteristic monitor transmitter 30, and a controller (e.g., controller 12) may be included with infusion device 34, as shown in FIG. 8(b). In example alternative embodiments, a pre-filter may be included with telemetered characteristic monitor transmitter 30, and a filter and calibrator may be included with a controller in an infusion device, as shown in FIG. 8(c). In other alternative example embodiments, a pre-filter may be included with telemetered characteristic monitor transmitter 30, while filter(s) and a calibrator are included in supplemental device 41, and a controller may be included in the infusion device, as shown in FIG. 8(d).

In particular example embodiments, a sensor system may generate a message that includes information based on a sensor signal such as digital sensor values, pre-filtered digital sensor values, filtered digital sensor values, calibrated digital sensor values, commands, and so forth, just to name a few examples. Such a message may include other types of information as well, including, by way of example but not limitation, a serial number, an ID code, a check value, values for other sensed parameters, diagnostic signals, other signals, and so forth. In particular example embodiments, digital sensor values Dsig may be filtered in a telemetered characteristic monitor transmitter 30, and filtered digital sensor values may be included in a message sent to infusion device 34 where the filtered digital sensor values may be calibrated and used in a controller. In other example embodiments, digital sensor values Dsig may be filtered and calibrated before transmission to a controller in infusion device 34. Alternatively, digital sensor values Dsig may be filtered, calibrated, and used in a controller to generate commands 22 that are sent from telemetered characteristic monitor transmitter 30 to infusion device 34.

In further example embodiments, additional components, such as a post-calibration filter, a display, a recorder, a blood glucose meter, etc. may be included in devices with any of the other components, or they may stand-alone. If a blood glucose meter is built into a device, for instance, it may be co-located in the same device that contains a calibrator. In alternative example embodiments, more, fewer, and/or different components may be implemented than those that are shown in FIGS. 8(a)-8(d) and/or described herein above.

In particular example embodiments, RF telemetry may be used to communicate between devices that contain one or more components, such as telemetered characteristic monitor transmitter 30 and infusion device 34. In alternative example embodiments, other communication mediums may be employed between devices, such as wireless wide area network (WAN) (e.g., cell communication), Wi-Fi, wires, cables, IR signals, laser signals, fiber optics, ultrasonic signals, and so forth, just to name a few examples.

Example Approaches to Glucose Sensor Signal Reliability Analysis

FIG. 9 is a schematic diagram of an example closed loop system 900 to control blood glucose levels via insulin infusion and/or glucagon infusion using at least a controller based on glucose level feedback via a sensor signal in accordance with an embodiment. In particular example embodiments, a closed loop control system may be used for delivering insulin to a body to compensate for β-cells that perform inadequately. There may be a desired basal blood glucose level $G_B$ for a particular body. A difference between a desired basal blood glucose level $G_B$ and an estimate of a present blood glucose level G is the glucose level error $G_E$ that may be corrected. For particular example embodiments, glucose level error $G_E$ may be provided as an input to controller 12, as shown in FIG. 9. Although at least a portion of controller 12 may be realized as a proportional-integral-derivative (PID) controller, claimed subject matter is not so limited, and controller 12 may be realized in alternative manners.

If glucose level error $G_E$ is positive (meaning, e.g., that a present estimate of blood glucose level G is higher than a desired basal blood glucose level $G_B$), then a command from controller 12 may generate a command 22 to drive insulin delivery system 34 to provide insulin 24 to body 20. Insulin delivery system 34 may be an example implementation of insulin delivery system 14 (e.g., of FIG. 1). Likewise, if $G_E$ is negative (meaning, e.g., that a present estimate of blood glucose level G is lower than a desired basal blood glucose level $G_B$), then a command from controller 12 may generate a command 22 to drive glucagon delivery system 35 to provide glucagon 25 to body 20. Glucagon delivery system 35 may be an example implementation of glucagon delivery system 15 (e.g., of FIG. 1).

Closed loop system 900 may also include and/or be in communication with a human interface 65. Example implementations for a human interface 65 are described herein above with particular reference to FIG. 1 in the context of an output device. As shown, human interface 65 may receive one or more commands 22 from controller 12. Such commands 22 may include, by way of example but not limitation, one or more commands to communicate information to a user (e.g., a patient, a healthcare provider, etc.) visually, audibly, haptically, some combination thereof, and so forth. Such information may include data, an alert, or some other notification 55. Human interface 65 may include a screen, a speaker, a vibration mechanism, any combination thereof, and so forth, just to name a few examples. Hence, in response to receiving a command 22 from controller 12, human interface 65 may present at least one notification 55 to a user via a screen, a speaker, a vibration, and so forth.

In terms of a control loop for purposes of discussion, glucose may be considered to be positive, and therefore insulin may be considered to be negative. Sensor 26 may sense an ISF glucose level of body 20 and generate a sensor signal 16. For certain example embodiments, a control loop may include a filter and/or calibration unit 456 and/or correction algorithm(s) 454. However, this is by way of example only, and claimed subject matter is not so limited. Sensor signal 16 may be filtered/or and calibrated at unit 456 to create an estimate of present blood glucose level 452. Although shown separately, filter and/or calibration unit 456 may be integrated with controller 12 without departing from claimed subject matter. Moreover, filter and/or calibration unit 456 may alternatively be realized as part of controller 12 (or vice versa) without departing from claimed subject matter.

In particular example embodiments, an estimate of present blood glucose level G may be adjusted with correction algorithms 454 before it is compared with a desired basal blood glucose level $G_B$ to calculate a new glucose level error $G_E$ to start a loop again. Also, an attendant, a caretaker, a patient, etc. may obtain blood glucose reference sample measurements from a patient's blood using, e.g., glucose test strips. These blood-based sample measurements may be used to calibrate ISF-based sensor measurements, e.g. using techniques such as those described in U.S. Pat. No. 6,895, 263, issued 17 May 2005, and/or other techniques. Although shown separately, a correction algorithms unit 454 may be integrated with controller 12 without departing from claimed subject matter. Moreover, correction algorithms unit 454 may alternatively be realized as part of controller 12 (or vice versa) without departing from claimed subject matter. Similarly, a difference unit and/or other functionality for calculating $G_E$ from G and $G_B$ may be incorporated as part of controller 12 without departing from claimed subject matter.

For an example PID-type of controller 12, if a glucose level error $G_E$ is negative (meaning, e.g., that a present estimate of blood glucose level is lower than a desired basal blood glucose level $G_B$), then controller 12 may reduce or stop insulin delivery depending on whether an integral component response of a glucose error $G_E$ is still positive. In alternative embodiments, as discussed below, controller 12 may initiate infusion of glucagon 25 if glucose level error $G_E$ is negative. If a glucose level error $G_E$ is zero (meaning, e.g., that a present estimate of blood glucose level is equal to a desired basal blood glucose level $G_B$), then controller 12 may or may not issue commands to infuse insulin 24 or glucagon 25, depending on a derivative component (e.g., whether a glucose level is rising or falling) and/or an integral component (e.g., how long and by how much a glucose level has been above or below basal blood glucose level $G_B$).

To more clearly understand the effects that a body has on such a control loop, a more detailed description of example physiological effects that insulin may have on glucose concentration in ISF is provided. In particular example embodiments, infusion delivery system 34 may deliver insulin into ISF of subcutaneous tissue 44 (e.g., also of FIGS. 3(a)-3(d), 4, and 6) of body 20. Alternatively, insulin delivery system 34 or a separate infusion device (e.g., glucagon delivery system 35) may similarly deliver glucose and/or glucagon into ISF of subcutaneous tissue 44. Here, insulin 24 may diffuse from local ISF surrounding a cannula into blood plasma and spread throughout body 20 in a main circulatory system (e.g., as represented by blood stream 47). Infused insulin may diffuse from blood plasma into ISF substantially throughout the entire body.

Here in the body, insulin 24 may bind with and activate membrane receptor proteins on cells of body tissues. This may facilitate glucose permeation into activated cells. In this way, tissues of body 20 may take up glucose from ISF. As ISF glucose level decreases, glucose may diffuse from blood plasma into ISF to maintain glucose concentration equilibrium. Glucose in ISF may permeate a sensor membrane of sensor 26 and affect sensor signal 16.

In addition, insulin may have direct and indirect effects on liver glucose production. Typically, increased insulin concentration may decrease liver glucose production. Therefore, acute and immediate insulin response may not only help a body to efficiently take up glucose, but it may also substantially stop a liver from adding to glucose in the blood stream. In alternative example embodiments, as pointed out above, insulin and/or glucose may be delivered more directly into the blood stream instead of into ISF, such as by delivery into veins, arteries, the peritoneal cavity, and so forth, just to name a few examples. Accordingly, any time delay associated with moving insulin and/or glucose from ISF into blood plasma may be diminished. In other alternative example embodiments, a glucose sensor may be in contact with blood or other body fluids instead of ISF, or a glucose sensor may be outside of a body such that it may measure glucose through a non-invasive means. Embodiments using alternative glucose sensors may have shorter or longer delays between an actual blood glucose level and a measured blood glucose level.

A continuous glucose measuring sensor (CGMS) implementation for sensor 26, for example, may detect a glucose concentration in ISF and provide a proportional current signal. A current signal (isig) may be linearly correlated with a reference blood glucose concentration (BG). Hence, a linear model, with two parameters (e.g., slope and offset), may be used to calculate a sensor glucose concentration (SG) from sensor current isig.

One or more controller gains may be selected so that commands from a controller 12 direct infusion device 34 to release insulin 24 into body 20 at a particular rate. Such a particular rate may cause insulin concentration in blood to follow a similar concentration profile as would be caused by fully functioning human β-cells responding to blood glucose concentrations in a body. Similarly, controller gain(s) may be selected so that commands 22 from controller 12 direct an infusion device of glucagon delivery system 35 to release glucagon 25 in response to insulin excursions. In particular example embodiments, controller gains may be selected at least partially by observing insulin response(s) of several normal glucose tolerant (NGT) individuals having healthy, normally-functioning β-cells.

In one or more example implementations, a system may additionally include a communication unit 458. A communication unit 458 may comprise, by way of example but not limitation, a wireless wide area communication module (e.g., a cell modem), a transmitter and/or a receiver (e.g., a transceiver), a Wi-Fi or Bluetooth chip or radio, some combination thereof, and so forth. Communication unit 458 may receive signals from, by way of example but not limitation, filter and/or calibration unit 456, sensor 26 (e.g., sensor signal 16), controller 12 (e.g. commands 22), any combination thereof, and so forth. Although not specifically shown in FIG. 9, communication unit 458 may also receive signals from other units (e.g., correction algorithms unit 454, a delivery system 34 and/or 35, human interface 65, etc.). Also, communication unit 458 may be capable of providing signals to any of the other units of FIG. 9 (e.g., controller 12, filter and/or calibration unit 456, human interface 65, etc.). Communication unit 458 may also be integrated with or otherwise form a part of another unit, such as controller 12 or filter and/or calibration unit 456.

Communication unit 458 may be capable of transmitting calibration output; calibration failure alarms; control algorithm states; sensor signal alerts; and/or other physiological, hardware, and/or software data (e.g., diagnostic data); and so forth to a remote data center for additional processing and/or storage (e.g., for remote telemetry purposes). These transmissions can be performed in response to discovered/detected conditions, automatically, semi-automatically (e.g., at the request of the remote data center), manually at the request of the patient, any combination thereof, and so forth, just to provide a few examples. The data can be subsequently served on request to remote clients including, but not limited to, mobile phones, physician's workstations, patient's desktop computers, any combination of the above, and so forth, just to name a few examples. Communication unit 458 may also be capable of receiving from a remote location various information, including but not limited to: calibration information, instructions, operative parameters, other control information, some combination thereof, and so forth. Such control information may be provided from communication unit 458 to other system unit(s) (e.g., controller 12, filter and/or calibration unit 456, etc.).

Figure 10:
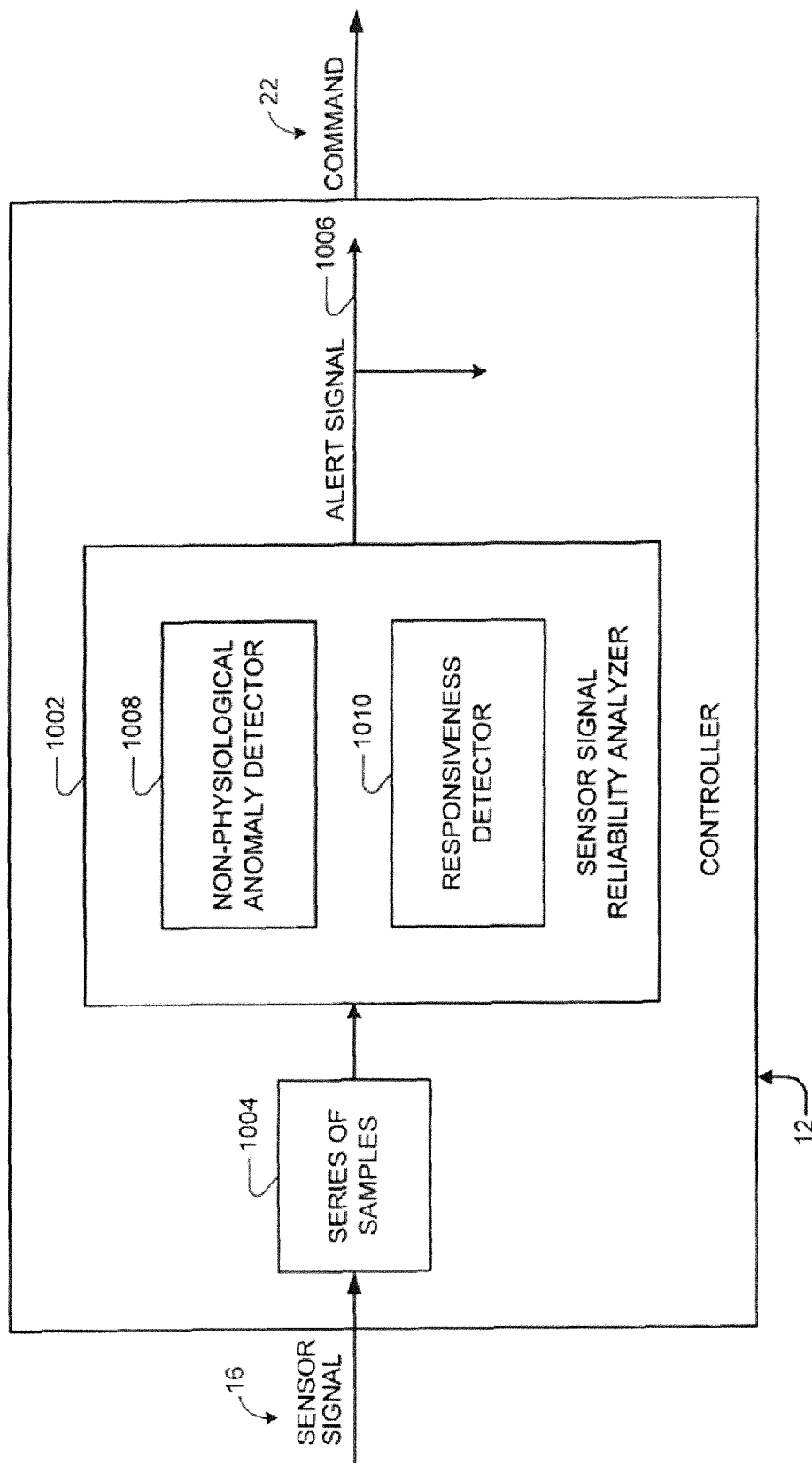
FIG. 10 is a schematic diagram of at least a portion of an example controller including a sensor signal reliability analyzer that may include a non-physiological anomaly detector and/or a responsiveness detector in accordance with an embodiment.

FIG. 10 is a schematic diagram of at least a portion of an example controller 12 including a sensor signal reliability analyzer 1002 that may include a non-physiological anomaly detector 1008 and/or a responsiveness detector 1010 in accordance with an embodiment. As illustrated, controller 12 may include a sensor signal reliability analyzer 1002, and controller 12 may include or have access to a series of samples 1004 and may produce at least one alert signal 1006.

For certain example embodiments, series of samples 1004 may comprise multiple samples taken from a sensor signal 16 (e.g., also of FIGS. 1 and 9) at multiple sampling times. Thus, series of samples 1004 may include multiple samples of at least one sensor signal, such as sensor signal 16, and may be responsive to a blood glucose level of a patient.

Sensor signal reliability analyzer 1002 may consider one or more facets of series of samples 1004 to assess at least one reliability aspect of a sensor signal. Based at least partly on such assessment(s), sensor signal reliability analyzer 1002 may produce at least one alert signal 1006. Such an alert signal 1006 may be issued when an assessment indicates that a sensor signal may not be sufficiently reliable so as to justify entrusting a patient's health to closed-loop glucose control decisions that are based on such an unreliable sensor signal. In example implementations, an alert signal 1006 may comprise at least one command 22 (e.g., also of FIGS. 1 and 9) that is issued from controller 12. For instance, an alert signal 1006 may be provided to a human interface 65 (e.g., of FIG. 9) and/or an insulin delivery system 34 (e.g., of FIG. 9). Alternatively and/or additionally, an alert signal 1006 may be provided to another component and/or unit of (e.g., that is internal of) controller 12.

An example sensor signal reliability analyzer 1002 of a controller 12 may include a non-physiological anomaly detector 1008 and/or a responsiveness detector 1010. In certain example embodiments, a non-physiological anomaly detector 1008 may consider one or more facets of series of samples 1004 to analyze at least one purity aspect of a sensor signal. An alert signal 1006 may be issued if an assessment indicates that a sensor signal may not be sufficiently pure inasmuch as it may additionally include artificial fluctuations that obscure a true blood glucose level valuation. By way of example only, one or more non-physiological anomalies may comprise artificial dynamics of at least one sensor signal that do not correlate with or otherwise represent blood glucose concentrations of a patient. In such situations, characterization of the one or more non-physiological anomalies may comprise detection of the artificial dynamics of the at least one sensor signal using the series of samples of the at least one sensor signal. Example embodiments for non-physiological anomaly detector 1008 are described further herein below with particular reference to FIGS. 11-13B.

In certain example embodiments, a responsiveness detector 1010 may consider one or more facets of series of samples 1004 to analyze at least one stability aspect of a sensor signal. An alert signal 1006 may be issued if an assessment indicates that a sensor signal may not be sufficiently stable inasmuch as it may be drifting away from a true blood glucose level valuation over time. By way of example only, an underlying trend of series of samples 1004 may reflect a potential divergence by the at least one sensor signal from a blood glucose level of a patient to an increasing extent over time due to a change in responsiveness of the at least one sensor signal to the blood glucose level of the patient. Example embodiments for responsiveness detector 1010 are described further herein below with particular reference to FIGS. 14-16C.

Figure 11:
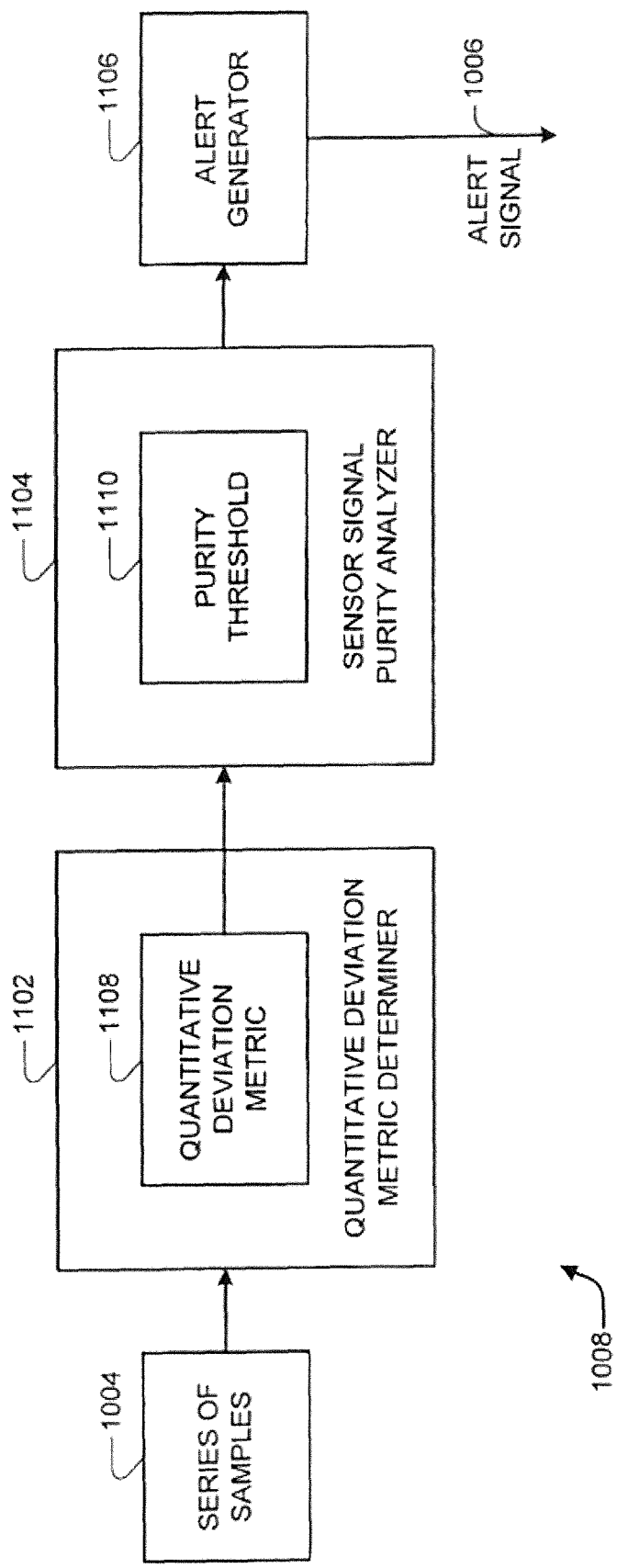
FIG. 11 is a schematic diagram of an example non-physiological anomaly detector that may include a sensor signal purity analyzer in accordance with an embodiment.

FIG. 11 is a schematic diagram of an example non-physiological anomaly detector 1008 that may include a sensor signal purity analyzer 1104 in accordance with an embodiment. As illustrated, non-physiological anomaly detector 1008 may include or have access to a series of samples 1004, a quantitative deviation metric determiner 1102, a sensor signal purity analyzer 1104, and an alert generator 1106. Quantitative deviation metric determiner 1102 may estimate a quantitative deviation metric 1108. Sensor signal purity analyzer 1104 may include at least one purity threshold 1110.

For certain example embodiments, series of samples 1004 may be provided to quantitative deviation metric determiner 1102. Series of samples 1004 may be obtained from at least one sensor signal (e.g., as shown in FIGS. 9 and 10), and the at least one sensor signal may be acquired from one or more subcutaneous glucose sensors (e.g., as shown in FIG. 9). Generally, a quantitative deviation metric determiner 1102 may determine at least one metric that quantitatively represents a deviation between a blood glucose level of a patient and at least one sensor signal.

More specifically, a quantitative deviation metric determiner 1102 may determine (e.g., calculate, estimate, ascertain, combinations thereof, etc.) at least one metric assessing a quantitative deviation (e.g., quantitative deviation metric 1108) based at least in part on series of samples 1004 to characterize one or more non-physiological anomalies of a representation of a blood glucose level of a patient by at least one sensor signal. In an example implementation, an at least one metric assessing a quantitative deviation may reflect an apparent reliability of at least one sensor signal that is generated by and acquired from one or more subcutaneous glucose sensors. In another example implementation, an at least one metric assessing a quantitative deviation may reflect a noise level of at least one sensor signal and/or an artifact level of the at least one sensor signal. Quantitative deviation metric 1108 may be provided to sensor signal purity analyzer 1104 (e.g., from quantitative deviation metric determiner 1102).

In example embodiments, a quantitative deviation metric 1108 may reflect whether and/or an extent to which a sensor signal is affected by non-physiological anomalies, such as noise, sensor artifacts, sudden signal dropouts, motion-related artifacts, lost transmissions, combinations thereof, and so forth, just to name a few examples. By way of example but not limitation, a quantitative deviation metric 1108 may be related to a variance or a derivative thereof. For example, a metric assessing a quantitative deviation may comprise a representation of a variance of a random factor in a signal and/or samples thereof. As another example, a metric assessing a quantitative deviation may comprise a representation of a variance expressed in a residual subspace produced by principal component analysis. However, these are merely examples of a metric assessing a quantitative deviation, and claimed subject matter is not limited in these respects.

A sensor signal purity analyzer 1104 may perform at least one purity assessment with respect to at least one sensor signal based at least in part on a metric assessing a quantitative deviation (e.g., quantitative deviation metric 1108). Such a purity assessment may comprise at least one comparison including a quantitative deviation metric 1108 and one or more purity thresholds 1110 (e.g., at least one predetermined threshold). If a purity of a sensor signal is impaired because one or more non-physiological anomalies are adversely affecting a representation of a blood glucose level of a patient by the sensor signal, then sensor signal purity analyzer 1104 may cause alert generator 1106 to issue an alert signal 1006.

Figure 12:
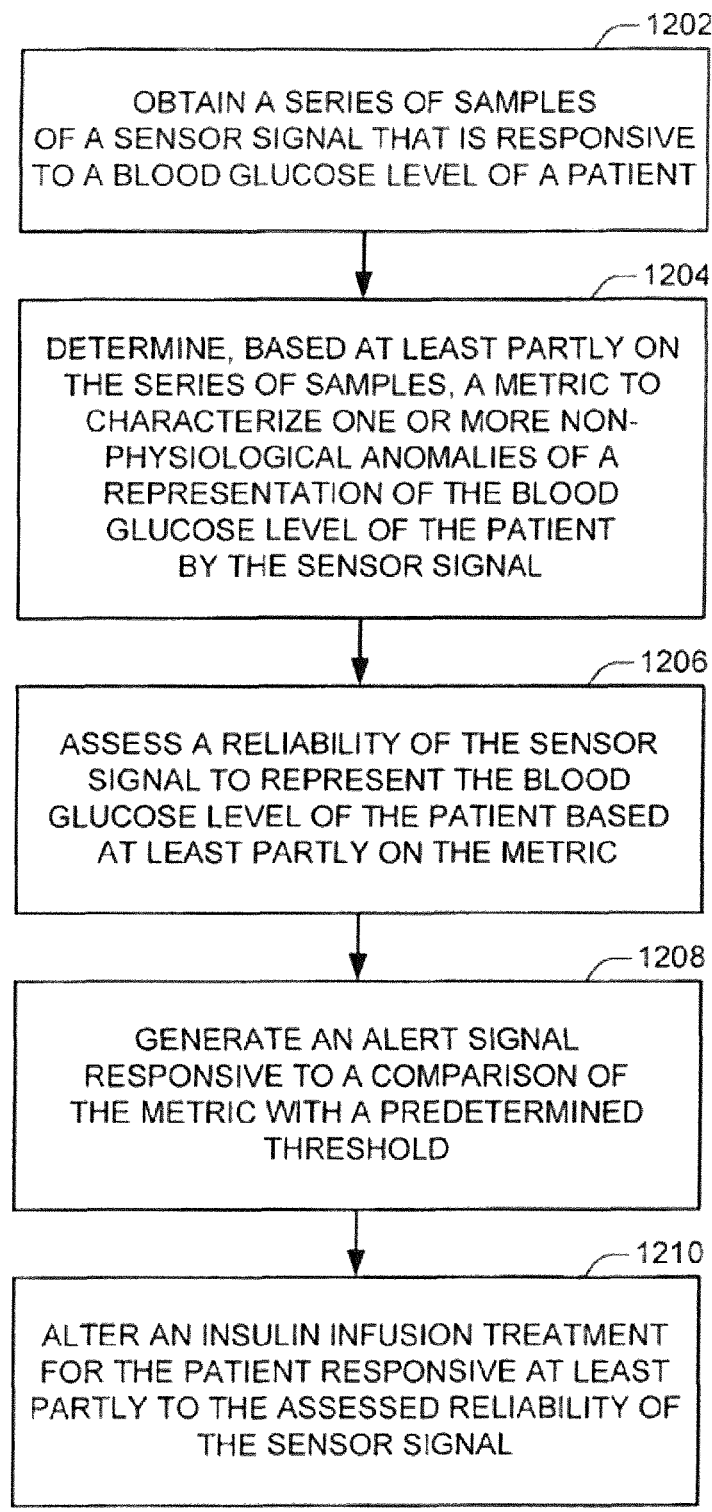
FIG. 12 is a flow diagram of an example method for handling non-physiological anomalies that may be present in a glucose sensor signal in accordance with an embodiment.

FIG. 12 is a flow diagram 1200 of an example method for handling non-physiological anomalies that may be present in a glucose sensor signal in accordance with an embodiment. As illustrated, flow diagram 1200 may include five operational blocks 1202-1210. Although operations 1202-1210 are shown and described in a particular order, it should be understood that methods may be performed in alternative orders and/or manners (including with a different number of operations) without departing from claimed subject matter. At least some operation(s) of flow diagram 1200 may be performed so as to be fully or partially overlapping with other operation(s). Additionally, although the description below may reference particular aspects and features illustrated in certain other figures, methods may be performed with other aspects and/or features.

For certain example implementations, at operation 1202, a series of samples of at least one sensor signal that is responsive to a blood glucose level of a patient may be obtained. At operation 1204, at least one metric may be determined, based at least partly on the series of samples of the at least one sensor signal, to characterize one or more non-physiological anomalies of a representation of the blood glucose level of the patient by the at least one sensor signal.

At operation 1206, a reliability of the at least one sensor signal to represent the blood glucose level of the patient may be assessed based at least partly on the at least one metric. At operation 1208, an alert signal may be generated responsive to a comparison of the at least one metric with at least one predetermined threshold. In an example implementation, an alert may be generated by initiating a signal to indicate to a blood glucose controller that a sensor that generated the at least one sensor signal was not functioning reliably for at least part of a time while the series of samples was being obtained. In another example implementation, an alert may be generated by presenting at least one human-perceptible indication that a sensor that generated the at least one sensor signal was not functioning reliably for at least part of a time while the series of samples was being obtained.

At operation 1210, an insulin infusion treatment for the patient may be altered responsive at least partly to the assessed reliability of the at least one sensor signal. For example, an insulin infusion treatment for a patient may be altered by changing (e.g., increasing or decreasing) an amount of insulin being infused, by ceasing an infusion of insulin, by delaying infusion until more samples are taken, by switching to a different sensor, by switching to a manual mode, by changing a relative weighting applied to a given sensor or sensors and/or the samples acquired there from, any combination thereof, and so forth, just to name a few examples.

For certain example implementations, a continuous glucose monitoring sensor may measure glucose concentration in ISF by oxidizing localized glucose with the help of a glucose-oxidizing enzyme. Sensor output may be a current signal (isig, nAmps) that is directly proportional to glucose concentration in ISF. Due to various reasons (e.g., immune response, motion artifact, pressure on sensor-area, localized depletion of glucose, etc.), sensor current may display sudden artificial dynamics which do not necessarily correlate with dynamics of actual blood glucose levels of a patient. Such artificial sensor dynamics may be classified as comprising or being related to sensor-noise and/or sensor-artifact(s).

One or more of various techniques may be implemented to detect such sensor-noise and/or artifacts. By way of example but not limitation, fault detection by dynamic principal component analysis (DPCA) is described below for detecting sensor-noise and/or sensor artifacts. PCA may use multivariate statistics to reduce a number of dimensions of source data by projecting it onto a lower dimensional space. PCA may include a linear transformation of original variables into a new set of variables that are uncorrelated to each other.

For an example implementation, let 'x' be a data vector. Here, 'x' may contain a time series of samples of sensor current as shown in equation (1):

$$x=[isig_t, isig_{t-1}, \ldots, isig_{t-n}] \quad (1)$$

where,
t: current sampling point
The data vector 'x' may be centered by its mean and scaled by dividing with its standard deviation as shown below in equation (2):

$$\bar{x} = \frac{x - x_{AVG}}{x_{STD}} \quad (2)$$

$$x_{STD} = \begin{cases} x_{LB}; & \text{if } x_{STD} < x_{LB} \\ x_{UB}; & \text{if } x_{STD} > x_{UB} \\ x_{STD}; & \text{otherwise} \end{cases}$$

where,
$x_{AVG}$: mean of x
$x_{STD}$: standard deviation of x which is bounded by lower-bound $x_{LB}$ and upperbound $x_{UB}$ A dynamic matrix may be created by stacking the data vector 'x' in the following manner:

$$Z = \begin{bmatrix} \bar{x}_t & \bar{x}_{t-1} & \cdots & \bar{x}_{t-h} \\ \bar{x}_{t-1} & \bar{x}_{t-2} & \cdots & \bar{x}_{t-h-1} \\ \vdots & \vdots & \ddots & \vdots \\ \bar{x}_{t+h-n} & \bar{x}_{t+h-n-1} & \cdots & \bar{x}_{t-n} \end{bmatrix} \quad (3)$$

A covariance of the Z-matrix (S) can be decomposed using singular value decomposition to obtain a matrix containing eigenvectors (P) (e.g., also known as a loading matrix) and a diagonal matrix containing the eigenvalues Λ, as shown below:

$$S = P \cdot \Lambda P^T \quad (4)$$

Such transformed data may be written as shown in equation (5):

$$y = P^T \cdot z \quad (5)$$

where,
$z = [\bar{x}_t, \bar{x}_{t-1}, \ldots, \bar{x}_{t-h}]^T$

Original data can be represented by a smaller number of principal components due to redundancy in data. This can result in one or more eigenvalues being equal to (or close to) zero. Consequently, the first 'k' (e.g., k may be equal to 2) eigenvalues, and their corresponding eigenvectors, may be used to form a PCA model, with other eigenvalues and eigenvectors being omitted. New scaled principal components may be written as shown in equation (6):

$$y = \Lambda_k^{-1/2} \cdot P_k^T \cdot z \quad (6)$$

Statistical quantities in a PCA model and a corresponding residual space may be checked by Hotelling's $T^2$ and/or Q statistics, respectively. $T^2$ statistics may indicate a quality of a model and may explain a normalized variance in a model subspace. Q statistics may indicate a size of a residual subspace and may represent a variance of random noise/artifacts expressed in the residual subspace.

Hotelling's $T^2$ statistic may be obtained by equation (7):

$$T^2 = y^T \cdot y \quad (7)$$

A Q statistic, which may be single-valued for each time point, for a residual subspace may be determined using equation (8):

$$Q = z^T \cdot (I - P_k \cdot P_k^T) \cdot z \quad (8)$$

When a Q statistic or statistics exceeds a predetermined (e.g., purity) threshold value (e.g., denoted $Q_{TH}$), one or more alerts may be issued indicating random sensor-noise and/or artifacts are present to a degree that indicates a sensor signal is unreliable.

In certain example implementations, determination of at least one metric may therefore include ascertaining a residual portion of at least one sensor signal based at least in part on a series of samples of the at least one sensor signal and determining at least one value associated with the residual portion of the at least one sensor signal.

In further example implementations, one or more principal components of the at least one sensor signal may be ascertained based at least in part on the series of samples of the at least one sensor signal. As such, the ascertaining of a residual portion may further include ascertaining the residual portion of the at least one sensor signal based at least in part on the ascertained one or more principal components. And, the determining of the at least one value associated with the residual portion may further include estimating a characteristic of random noise expressed in a subspace associated with the residual portion of the at least one sensor signal, with the characteristic comprising one or more values descriptive of how data are distributed with respect to an average of the data.

Figure 13A:
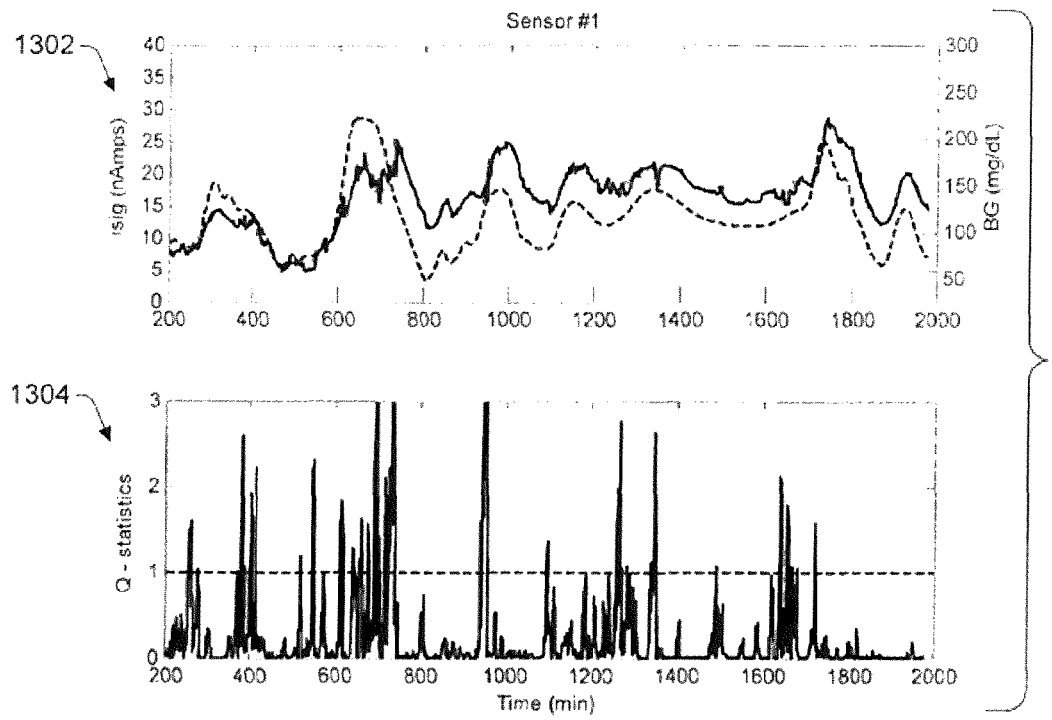
FIGS. 13A and 13B depict graphical diagrams that illustrate example comparisons between sensor signal values and measured blood glucose values in relation to non-physiological anomalies for first and second sensors, respectively, in accordance with an embodiment.
Figure 13B:
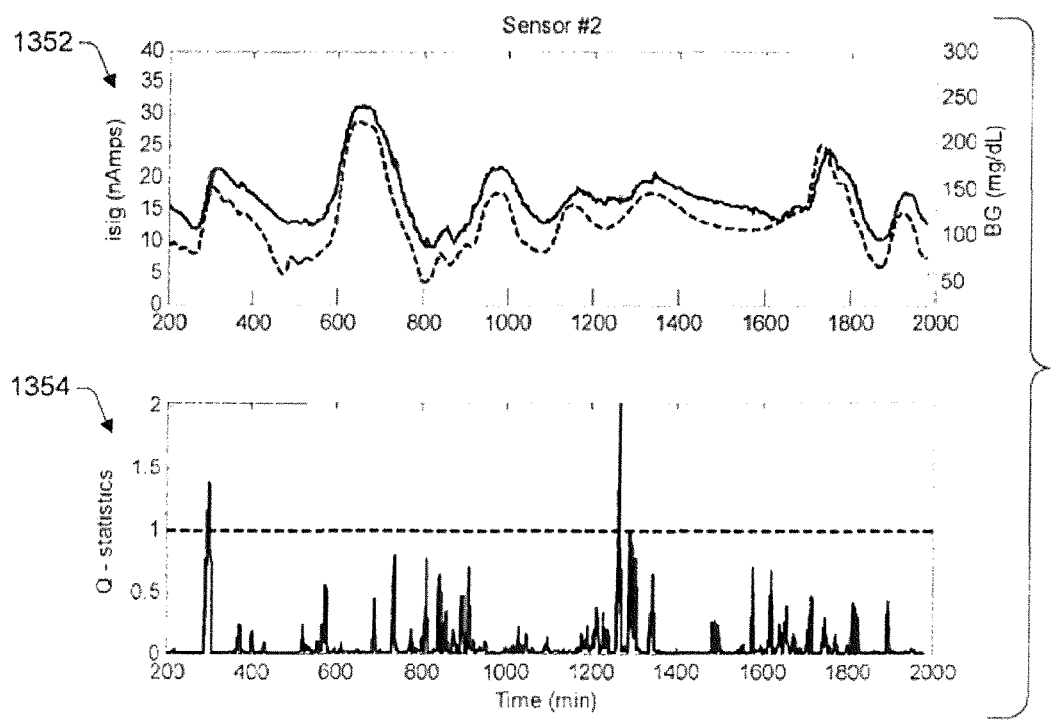

FIGS. 13A and 13B depict graphical diagrams 1300 and 1350 that illustrate example comparisons between sensor signal values and measured blood glucose values in relation to non-physiological anomalies for first and second sensors, respectively, in accordance with an embodiment. As illustrated, graphical diagrams 1300 (e.g., graphs 1302 and 1304) correspond to a first sensor. Graphical diagrams 1350 (e.g., graphs 1352 and 1354) correspond to a second sensor.

To develop data for graphical diagrams 1300 and 1350, retrospective sensor fault analysis was performed on data obtained from a closed-loop clinical experiment. Two sensors were inserted on a type 1 diabetic subject, and data was collected for 36 hours. Sensor current (isig) is plotted along with interpolated blood glucose (BG) concentration obtained from a glucose analyzer (also known as YSI).

As shown, along the abscissa axis of all four graphs 1302, 1304, 1352, and 1354, time (minutes) is depicted extending from 200 to 2000. Graphs 1302 and 1352 depict isig (nAmps) from 0 to 40 along a left ordinate axis and depict BG (mg/dL) from 0 to 300 along a right ordinate axis. Graphs 1304 and 1354 depict Q statistics from 0 to 3 and from 0 to 2, respectively, along an ordinate axis. A dashed line runs horizontally along graphs 1304 and 1354 at Q=1 (e.g., an example of $Q_{TH}$).

In graphs 1302 and 1352, solid lines represent current sensor signal values (isig), and dashed lines represent measured blood glucose (BG). In graphs 1304 and 1354, solid lines represent values for Q statistics. Circles or dots in graphs 1302 and 1352 indicate time-points when Q-statistics exceed a predetermined threshold value (e.g., $Q_{TH}=1$). By comparing times having relatively higher Q statistical values (e.g., above the dashed line at $Q_{TH}=1$) in graphs 1304 and 1354 to the solid lines of graphs 1302 and 1352, respectively, it is apparent that higher Q values correspond to times when the solid lines deviate more rapidly with respect to the dashed lines due to impurities in the sensor signal. It also appears that sensor 1 (of graphical diagrams 1300) was noisier than sensor 2 (of graphical diagrams 1350) during the closed-loop clinical experiment.

Figure 14:
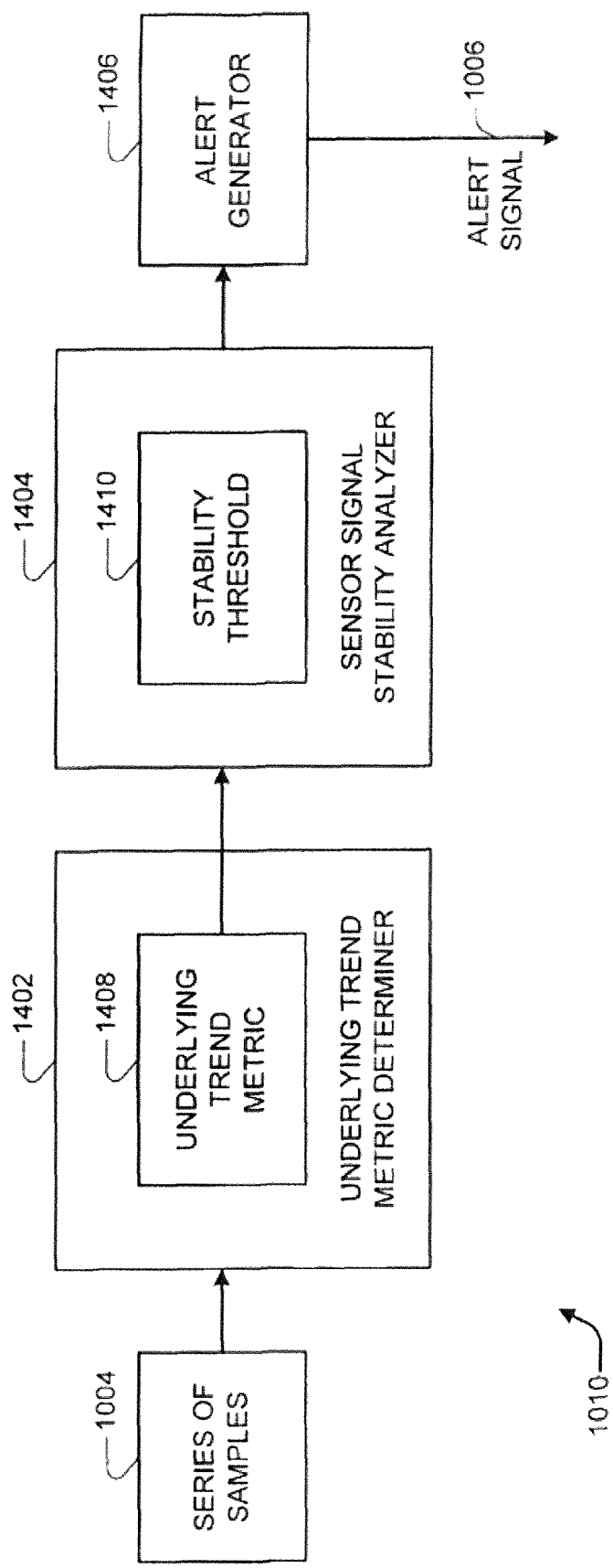
FIG. 14 is a schematic diagram of an example responsiveness detector that may include a sensor signal stability analyzer in accordance with an embodiment.

FIG. 14 is a schematic diagram of an example responsiveness detector 1010 that may include a sensor signal stability analyzer 1404 in accordance with an embodiment. As illustrated, responsiveness detector 1010 may include or have access to a series of samples 1004, an underlying trend metric determiner 1402, a sensor signal stability analyzer 1404, and an alert generator 1406. Underlying trend metric determiner 1402 may estimate an underlying trend metric 1408. Sensor signal stability analyzer 1404 may include at least one stability threshold 1410.

For certain example embodiments, series of samples 1004 may be provided to underlying trend metric determiner 1402. Series of samples 1004 may be obtained from at least one sensor signal (e.g., as shown in FIGS. 9 and 10), and the at least one sensor signal may be acquired from one or more subcutaneous glucose sensors (e.g., as shown in FIG. 9).

An underlying trend metric determiner 1402 may determine (e.g., calculate, estimate, ascertain, combinations thereof, etc.) at least one metric assessing an underlying trend (e.g., underlying trend metric 1408) based at least in part on series of samples 1004 to identify a change in responsiveness of at least one sensor signal to blood glucose levels of a patient over time. Underlying trend metric 1408 may be provided to sensor signal stability analyzer 1404 (e.g., from underlying trend metric determiner 1402).

In example embodiments, an underlying trend metric 1408 may reflect whether and/or an extent to which a sensor signal is affected by an unstable sensor, such as a sensor that has a changing responsiveness to blood glucose levels of a patient over time. For instance, a glucose sensor may diverge from sensing an accurate glucose level over time (e.g., that diverges upward or downward due to drift). By way of example but not limitation, an underlying trend metric 1408 may be related to a fundamental, long-term, overall, etc. trend of sensor data and/or values sampled from such sensor data. For example, a metric assessing an underlying trend may comprise a monotonic curve derived from sampled data, an iteratively grown trend value, combinations thereof, and so forth, just to name a couple of examples. As another example, a metric assessing an underlying trend may comprise a slope of a linear regression applied to sampled data, a slope of a linear regression applied to a monotonic curve, some combination thereof, and so forth, just to name a couple of examples. However, these are merely examples of a metric assessing an underlying trend, and claimed subject matter is not limited in these respects.

A sensor signal stability analyzer 1404 may perform at least one stability assessment with respect to at least one sensor signal based at least in part on a metric assessing an underlying trend (e.g., underlying trend metric 1408). Such a stability assessment may comprise at least one comparison of an underlying trend metric 1408 with one or more stability thresholds 1410 (e.g., at least one predetermined threshold). By way of example only, a stability assessment may include comparing at least one metric assessing an underlying trend with at least a first predetermined threshold and a second predetermined threshold.

In example implementations including first and second predetermined thresholds, performance of a stability assessment may include assessing a reliability of at least a sensor signal as being in a first state (e.g., a stable state), a second state (e.g., an unstable and drifting state), or a third state (e.g., an unstable and dying state). For example, a reliability of at least one sensor signal may be assessed to be in a first state responsive to a comparison of at least one metric assessing an underlying trend with a first predetermined threshold. A reliability of at least one sensor signal may be assessed to be in a second state responsive to a comparison of at least one metric assessing an underlying trend with a first predetermined threshold and a second predetermined threshold. A reliability of at least one sensor signal may be assessed to be in a third state responsive to a comparison of at least one metric assessing an underlying trend with a second predetermined threshold.

If a responsiveness of a sensor signal is assessed to be changing, then sensor signal stability analyzer 1404 may cause alert generator 1406 to issue an alert signal 1006. In an alternative implementation, non-physiological anomaly detector 1008 and responsiveness detector 1010 may share an alert generator (e.g., alert generator 1106 (of FIG. 11) and alert generator 1406 may comprise a single alert generator).

Figure 15:
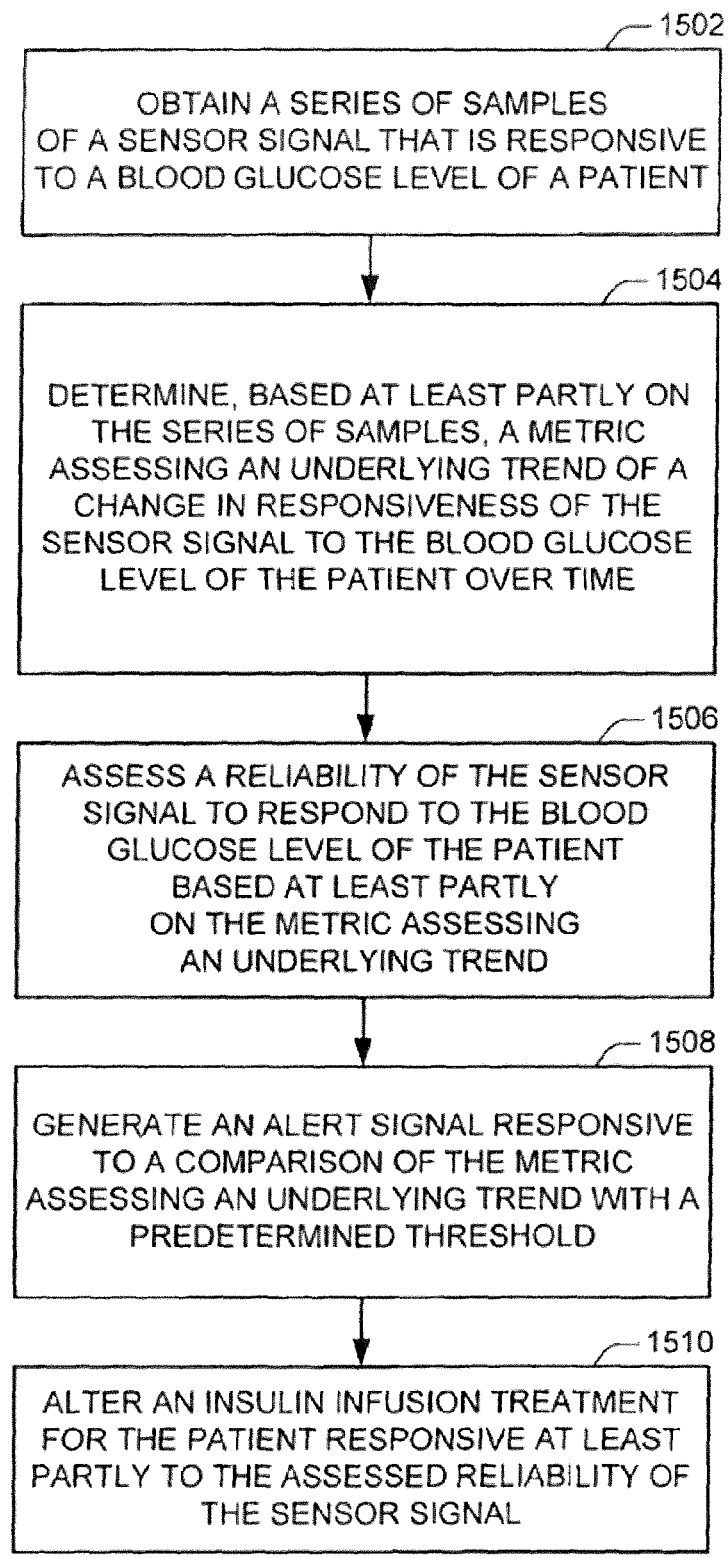
FIG. 15 is a flow diagram of an example method for handling apparent changes in responsiveness of a glucose sensor signal to blood glucose levels of a patient in accordance with an embodiment.

FIG. 15 is a flow diagram 1500 of an example method for handling apparent changes in responsiveness of a glucose sensor signal to blood glucose levels in a patient in accordance with an embodiment. As illustrated, flow diagram 1500 may include five operational blocks 1502-1510. Although operations 1502-1510 are shown and described in a particular order, it should be understood that methods may be performed in alternative orders and/or manners (including with a different number of operations) without departing from claimed subject matter. At least some operation(s) of flow diagram 1500 may be performed so as to be fully or partially overlapping with other operation(s). Additionally, although the description below may reference particular aspects and features illustrated in certain other figures, methods may be performed with other aspects and/or features.

For certain example implementations, at operation 1502, a series of samples of at least one sensor signal that is responsive to a blood glucose level of a patient may be obtained. At operation 1504, at least one metric assessing an underlying trend may be determined, based at least in part on the series of samples of the at least one sensor signal, to identify whether the at least one sensor signal appears is changing a responsiveness to the blood glucose level of the patient over time.

At operation 1506, a reliability of the at least one sensor signal to respond to the blood glucose level of the patient may be assessed based at least partly on the at least one metric assessing an underlying trend. For example, a comparison of the at least one metric assessing an underlying trend with at least one predetermined threshold may be performed. At operation 1508, an alert signal may be generated responsive to a comparison of the at least one metric assessing an underlying trend with at least one predetermined threshold.

At operation 1510, an insulin infusion treatment for the patient may be altered responsive at least partly to the assessed reliability of the at least one sensor signal. For example, an insulin infusion treatment for a patient may be altered by changing (e.g., increasing or decreasing) an amount of insulin being infused, by ceasing an infusion of insulin, by delaying infusion until more samples are taken, by switching to a different sensor, by switching to a manual mode, by changing a relative weighting applied to a given sensor or sensors and/or the samples acquired there from, any combination thereof, and so forth, just to name a few examples.

In certain example implementations, a subcutaneous glucose sensor may measure the glucose level in body fluid. An electro-chemical glucose sensor may generate current at a nanoAmp level. An amplitude of such current may change based on a glucose level in the body fluid; hence, glucose measurement may be performed. Glucose sensors may be designed to stay in a body for, for example, several days. Unfortunately, a signal provided from some sensors may gradually drift down (or up) (e.g., a current level may gradually drift higher or lower), and such a signal may eventually die out due to sensor defects, environmental factors, or other issues. Sensor fault detection may therefore involve determining whether a signal from a sensor has become unreliable due to a drifting of the signal, such that the signal increasingly diverges further from actual physiological activity of a patient's blood glucose level.

Figure 16A:
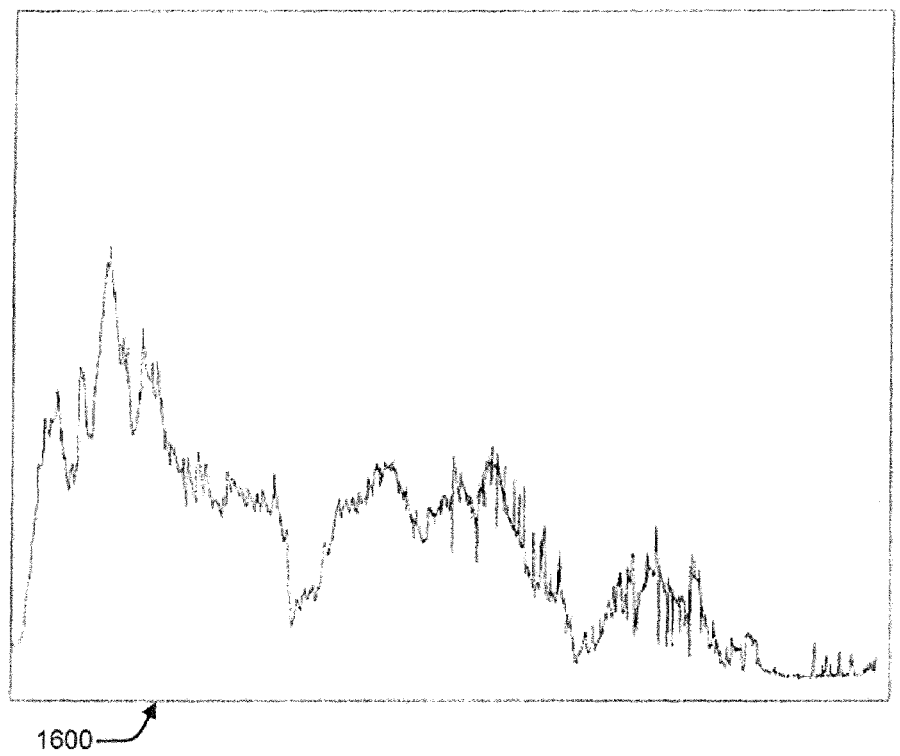
FIG. 16A depicts a graphical diagram that illustrates an example of a downward drifting sensor signal along with physiological activity in accordance with an embodiment.

FIG. 16A depicts a graphical diagram 1600 that illustrates an example of a downward drifting sensor signal along with physiological activity in accordance with an embodiment. Because an overall sensor signal from a sensor is drifting downward while a blood glucose level is not, a response to physiological activity by the sensor may be considered to be unstable and/or dying. The sensor signal appears to be diverging from an actual blood glucose level to an increasing extent as time elapses.

For certain example implementations, detection of such diverging (e.g., drifting) of a sensor signal may include two phases. A first phase may include trend estimation in which an underlying signal trend (e.g., a fundamental, overall, long-term, etc. trend) of a sensor signal is determined. A second phase may include performing an assessment (e.g., a stability analysis) to determine whether an estimated underlying trend indicates drifting of the sensor signal.

Any one or more of multiple different approaches may be implemented to estimate an underlying signal trend. Three example implementation approaches for trend estimation are described below: empirical mode decomposition, wavelet decomposition, and iterative trend estimation. With an example implementation of empirical mode decomposition, at least one metric assessing an underlying trend may be determined by decomposing at least one sensor signal as represented by a series of samples using spline functions to remove relatively higher frequency components from the at least one sensor signal. With an example implementation of wavelet decomposition, at least one metric assessing an underlying trend may be determined by decomposing at least one sensor signal as represented by a series of samples using at least one discrete wavelet transform and reconstructing a smoothed signal from one or more approximation coefficients resulting from the at least one discrete wavelet transform. With an example implementation of iterative trend estimation, at least one metric assessing an underlying trend may be determined by iteratively updating a trend estimation at multiple samples of a series of samples of at least one sensor signal based at least partly on a trend estimation at a previous sample and a growth term.

First, an example of empirical mode decomposition (EMD) is described. EMD may be based on an initial part of a Hilbert-Huang Transform (HHT). HHT is designed to perform "instantaneous" frequency estimation for nonlinear, non-stationary signals. EMD may be used for signal decomposition in HHT. In EMD, spline functions may be used to gradually remove details from an original signal. Such a procedure may be repeated until a monotonic curve or a curve with but one extreme value remains. Such a monotonic (e.g., smooth) curve may be considered an example of an estimation of an underlying trend and/or underlying trend metric for a signal. A linear regression may be performed on a monotonic curve. A slope of such a linear regression may represent a quantitative measurement of a signal trend (Tr) of a sensor signal and may be considered an example of an estimated underlying trend metric.

Second, an example of wavelet decomposition is described. In wavelet decomposition, a discrete wavelet transform (DWT) may be used to decompose a signal into different levels of details. A detail level having a smoothest signal may be considered an approximation signal, which can be reconstructed from approximation coefficients calculated from a DWT. A smooth signal that is reconstructed from approximation coefficients may be considered an example of an estimation of an underlying trend and/or underlying trend metric for a signal. A linear regression may be performed on an approximation signal. A slope of such a linear regression may represent a quantitative measurement of a signal trend (Tr) of a sensor signal and may be considered an example of an estimated underlying trend metric.

Figure 16B:
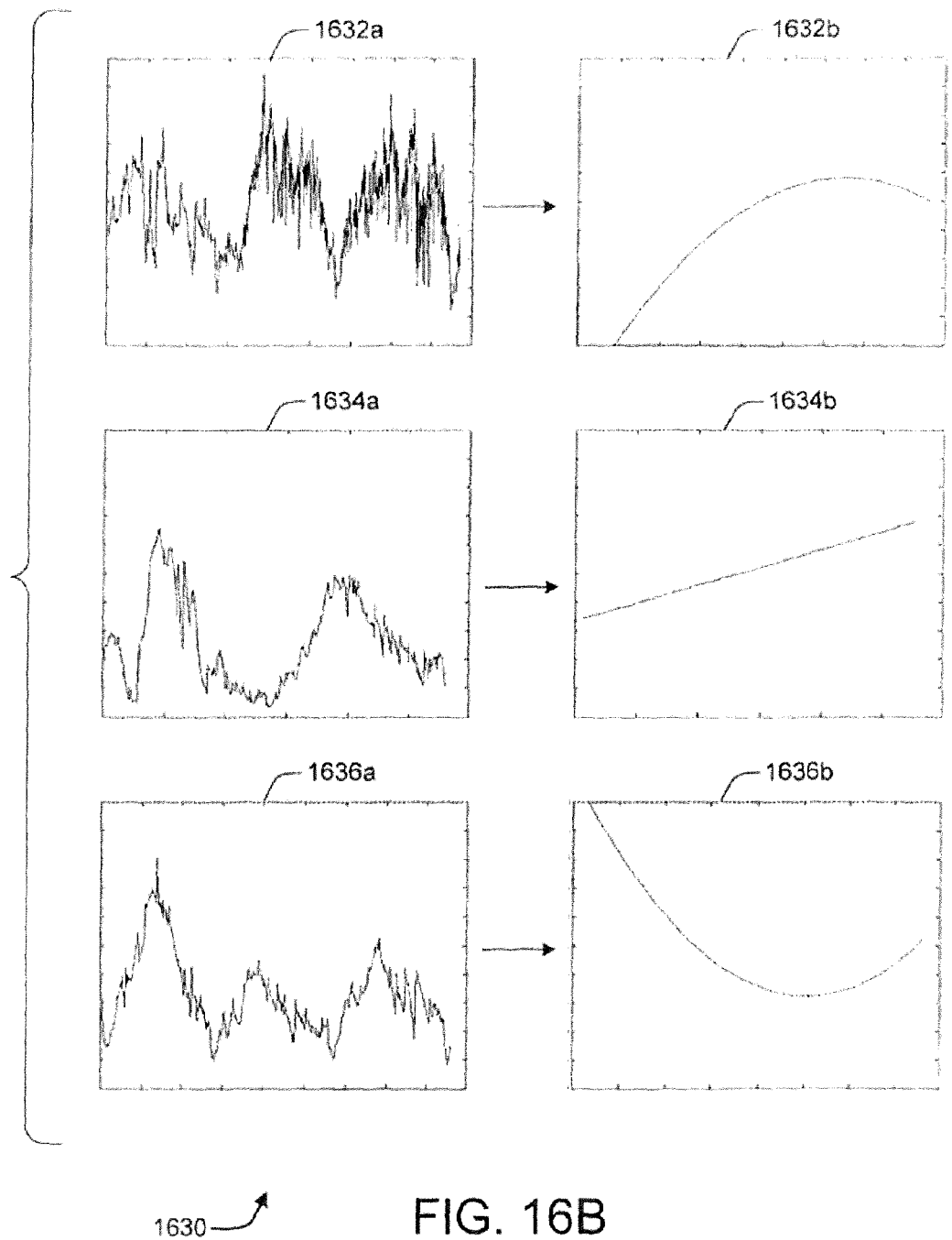
FIGS. 16B and 16C depict graphical diagrams that illustrate multiple example glucose signals and corresponding monotonic fundamental signal trends as generated by first and second example signal trend analysis approaches, respectively, in accordance with an embodiment.
Figure 16C:
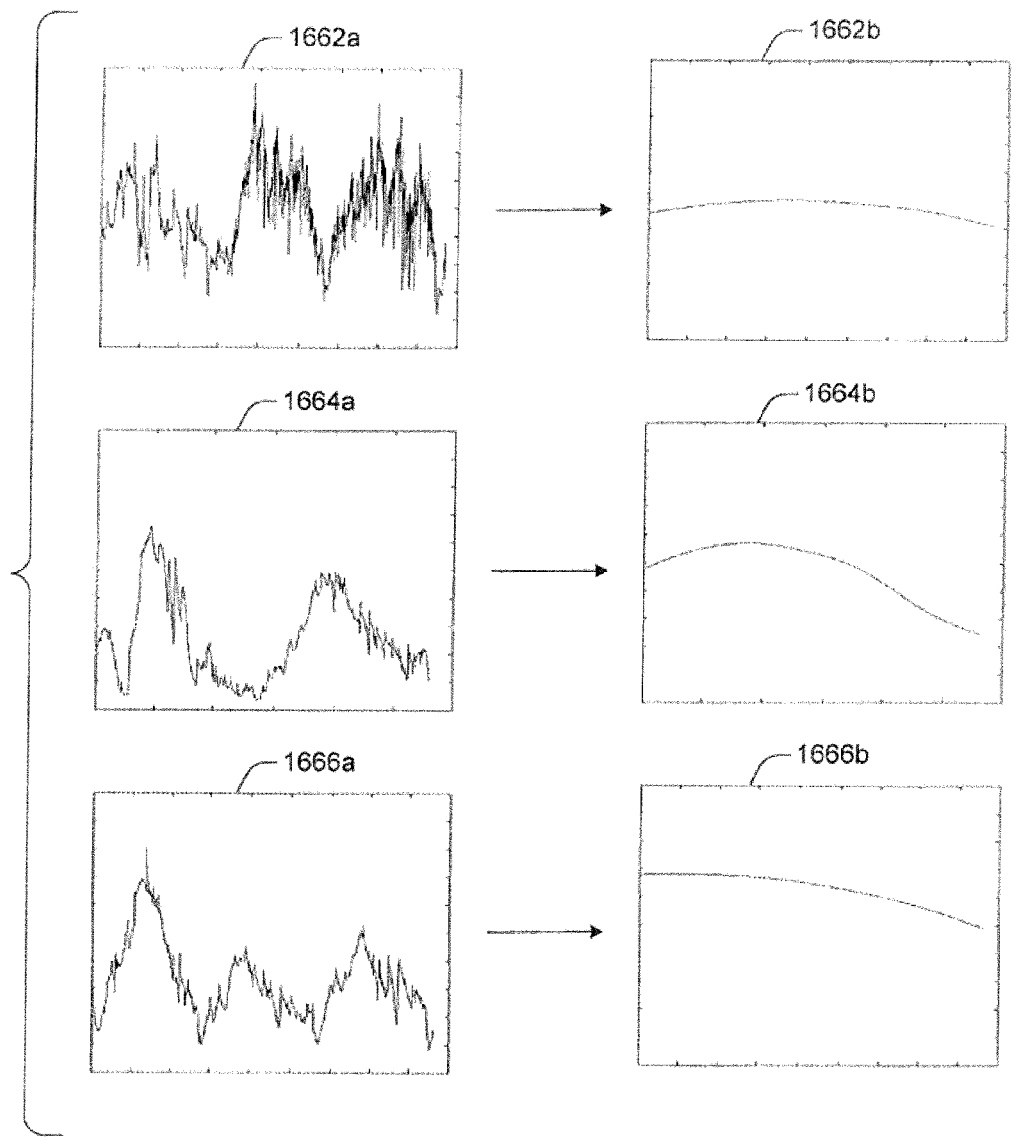

FIGS. 16B and 16C depict graphical diagrams 1630 and 1660, respectively, that illustrate multiple example glucose signals and corresponding monotonic fundamental signal trends as generated by first and second example signal trend analysis approaches, respectively, in accordance with an embodiment. Graphical diagrams 1630 correspond to an example EMD approach, and graphical diagrams 1660 correspond to an example wavelet decomposition approach.

Graphs 1632a, 1634a, and 1636a and graphs 1662a, 1664a, and 1666a depict example signals from a glucose sensor. Graphs 1632b, 1634b, and 1636b depict example respective corresponding monotonic fundamental signal trends generated by an example EMD approach. Graphs 1662b, 1664b, and 1666b depict example respective corresponding monotonic fundamental signal trends generated by an example wavelet decomposition approach via smoothed signals that are reconstructed from approximation coefficients.

In example implementations, at least one metric assessing an underlying trend may be determined by producing the at least one metric assessing an underlying trend using a slope of a linear regression that is derived at least partly from a series of samples of the at least one sensor signal. In further example implementations, a series of samples of at least one sensor signal may be transformed to derive a monotonic curve, and production of at least one metric assessing an underlying trend may include calculating a slope of a linear regression, with the linear regression being derived at least partly from the monotonic curve.

Third, an example of iterative trend estimation is described. In iterative trend estimation, a trend at each signal sample n may be iteratively calculated based on a trend at a previous signal sample n−1. An initial trend can be estimated by linear regression. A slope of a linear regression may be considered as an initial trend Tr(0). An intercept of a linear regression may be considered as initial growth Gr(0). A trend at each point may be estimated as follows using equation (9):

$$Tr(n)=Tr(n-1)+Wg \times Gr(n-1). \quad (9)$$

In equation (9), Gr(n) may be considered a growth term, and Wg may be considered a growth parameter, which can be determined empirically. Growth term Gr(n) may be iteratively updated as well, as shown by equation (10):

$$Gr(n)=Wg \times Gr(n-1)+Wt[sig(n)-Tr(n)], \quad (10)$$

where Wt may be considered a trend parameter, which can be determined empirically.

Example approaches for a first phase to estimate an underlying signal trend are described above with regard to EMD, wavelet decomposition, and iterative trend estimation. Example approaches for a second phase to determine whether an estimated underlying trend indicates drifting of a sensor signal are described below.

For an example second phase, at least one assessment may be performed to decide whether a determined trend Tr(n) at signal sample n indicates a changing responsiveness of a sensor signal to blood glucose levels of a patient (e.g., a drifting of the sensor signal). Such a trend value may be determined using any one or more of the above-three described example implementations and/or an alternative approach.

In an example implementation for a second phase, two positive stability thresholds T1 and T2 (e.g., a first and a second predetermined threshold) may be used for drift detection, where T1<T2, to establish three example detection categories: normal operation, drifting, and dying. However, one stability threshold to determine an affirmative or negative drifting decision may alternatively be implemented without departing from claimed subject matter. If an absolute value of trend Tr(n) is less than T1, a sensor trend may be deemed to be within normal fluctuations. Thus, no drifting may be declared in such circumstances, and/or a sensor may be considered stable. In such circumstances, a drifting factor F may be set, by way of example only, to zero (0).

If an absolute value of trend Tr(n) is between T1 and T2, a sensor trend may be deemed to be outside of normal fluctuations, and/or a sensor may be considered to be unstable and drifting. Hence, drifting may be declared. A severity of such drifting may be measured by a drifting factor F as shown, by way of example only, in equation (11):

$$F = \frac{\text{abs}[Tr(n)] - T1}{T2 - T1}. \quad (11)$$

Drifting factor F may be set to have a value range between 0 and 1. The larger a drifting factor F value, the more severe a drifting may be considered to be. However, drifting factor(s) may be calculated in alternative manners without departing from claimed subject matter. In an example implementation, at least one value indicating a severity of divergence by at least one sensor signal from a blood glucose level of a patient over time may be ascertained based at least partly on at least one metric assessing an underlying trend, a first predetermined threshold, and a second predetermined threshold. Also, if an absolute value of trend Tr(n) is greater than T2, a sensor may be considered unstable and may be declared to be dying due to severe drifting. In such circumstances, a drifting factor F may be set, by way of example only, to one (1).

Figure 17:
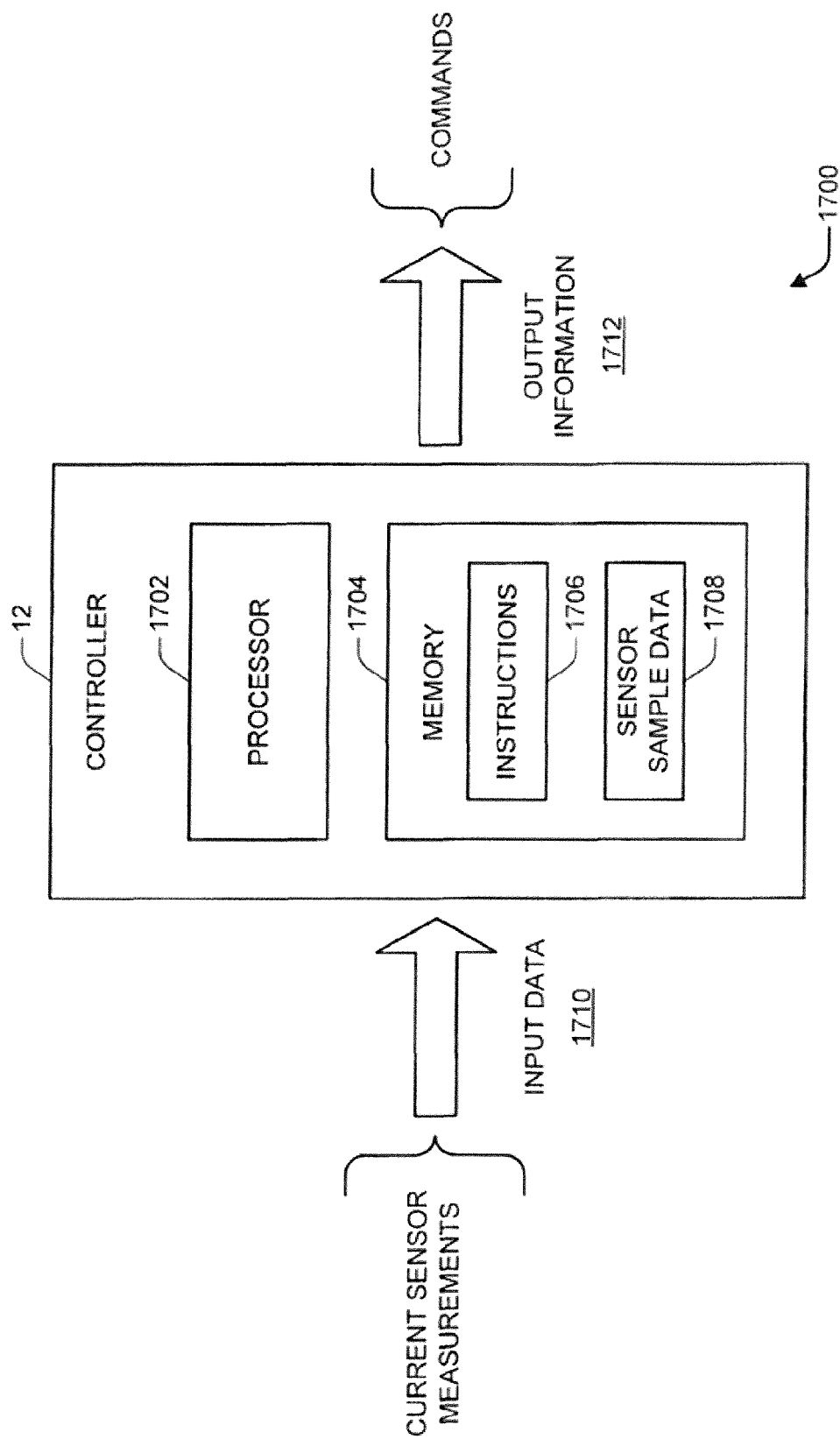
FIG. 17 is a schematic diagram of an example controller that produces output information based on input data in accordance with an embodiment.

FIG. 17 is a schematic diagram 1700 of an example controller 12 that produces output information 1712 based on input data 1710 in accordance with an embodiment. As illustrated, controller 12 may include one or more processors 1702 and at least one memory 1704. In certain example embodiments, memory 1704 may store or otherwise include instructions 1706 and/or sensor sample data 1708. Sensor sample data 1708 may include, by way of example but not limitation, blood glucose sensor measurements, such as series of samples 1004 (e.g. of FIGS. 10, 11, and 14).

In particular example implementations, controller 12 of FIG. 17 may correspond to a controller 12 of FIGS. 1, 9, and/or 10. Input data 1710 may include, for example, sensor measurements (e.g., from an ISF current sensor). Output information 1712 may include, for example, one or more commands, and such commands may include reporting information. Current sensor measurements of input data 1710 may correspond to sensor signal 16 (e.g., of FIGS. 1, 9, and 10) and/or sampled values resulting there from. Commands of output information 1712 may correspond to commands 22 (e.g., of FIGS. 1, 9, and 10), which may be derived from one or more alert signals 1006 (e.g., of FIGS. 10, 11, and 14) and/or instructions or other information resulting there from.

In certain example embodiments, input data 1710 may be provided to controller 12. Based on input data 1710, controller 12 may produce output information 1712. Current sensor measurements that are received as input data 1710 may be stored as sensor sample data 1708. Controller 12 may be programmed with instructions 1706 to perform algorithms, functions, methods, etc.; to implement attributes, features, etc.; and so forth that are described herein. For example, a controller 12 may be configured to perform the functions described herein with regard to a non-physiological anomaly detector 1008 and/or a responsiveness detector 1010 (e.g., of FIGS. 10, 11, and/or 14). Controller 12 may therefore be coupled to at least one blood glucose sensor to receive one or more signals based on blood glucose sensor measurements.

A controller 12 that comprises one or more processors 1702 may execute instructions 1706 to thereby render a controller unit a special purpose computing device to perform algorithms, functions, methods, etc.; to implement attributes, features, etc.; and so forth that are described herein. Processor(s) 1702 may be realized as microprocessors, digital signal processors (DSPs), application specific integrated circuits (ASICs), programmable logic devices (PLDs), controllers, micro-controllers, a combination thereof, and so forth, just to name a few examples. Alternatively, an article may comprise at least one storage medium (e.g., such as one or more memories) having stored thereon instructions 1706 that are executable by one or more processors.

Unless specifically stated otherwise, as is apparent from the preceding discussion, it is to be appreciated that throughout this specification discussions utilizing terms such as "processing", "computing", "calculating", "determining", "assessing", "estimating", "identifying", "obtaining", "representing", "receiving", "transmitting", "storing", "analyzing", "measuring", "detecting", "controlling", "delaying", "initiating", "providing", "performing", "generating", "altering" and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular example embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be understood that aspects described above are examples only and that embodiments may differ there from without departing from claimed subject matter. Also, it should be noted that although aspects of the above systems, methods, apparatuses, devices, processes, etc. have been described in particular orders and in particular arrangements, such specific orders and arrangements are merely examples and claimed subject matter is not limited to the orders and arrangements as described. It should additionally be noted that systems, devices, methods, apparatuses, processes, etc. described herein may be capable of being performed by one or more computing platforms.

In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may comprise one or more storage articles and/or devices for storing machine-readable instructions or information. Such storage articles and/or devices may comprise any one of several media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although there have been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A method comprising:

obtaining a series of samples of at least one sensor signal that is responsive to a blood glucose level of a patient wherein the at least one sensor signal is generated by a glucose sensor during a time that the glucose sensor is in contact with the patient;

determining, using the series of samples and using one or more processors, at least one metric assessing an underlying trend of a change in responsiveness of the at least one sensor signal to the blood glucose level of the patient over time;

assessing a reliability of the at least one sensor signal to respond to the blood glucose level of the patient using the at least one metric assessing the underlying trend and using the one or more processors; and in response to the assessing the reliability of the at least one sensor signal, altering an infusion treatment for the patient, or transmitting notification to the patient or a healthcare provider indicative of the reliability of the at least one sensor signal, wherein the assessing the reliability of the at least one sensor signal comprises comparing the at least one metric with at least a first predetermined threshold and a second predetermined threshold, wherein the at least one sensor signal is assessed to not be drifting or the at least one sensor is assessed to be stable, or both, if an absolute value of the underlying trend is less than the first predetermined threshold, wherein the at least one sensor signal is assessed to be drifting or the at least one sensor is assessed to be unstable, or both, if the absolute value of the underlying trend is between the first and second predetermined thresholds, wherein the at least one sensor is assessed to be dying, if the absolute value of the underlying trend is greater than the second predetermined threshold, and wherein the determining of the at least one metric assessing the underlying trend comprises determining the at least one metric using a slope of a linear regression that is derived at least partly from the series of samples of the at least one sensor signal.

2. A method comprising:

obtaining a series of samples of at least one sensor signal that is responsive to a blood glucose level of a patient wherein the at least one sensor signal is generated by a glucose sensor during a time that the glucose sensor is in contact with the patient;

transforming the series of samples of the at least one sensor signal to derive a monotonic curve;

determining, using the series of samples and using one or more processors, at least one metric assessing an underlying trend of a change in responsiveness of the at least one sensor signal to the blood glucose level of the patient over time;

assessing a reliability of the at least one sensor signal to respond to the blood glucose level of the patient using the at least one metric assessing the underlying trend and using the one or more processors; and in response to the assessing the reliability of the at least one sensor signal, altering an infusion treatment for the patient, or transmitting notification to the patient or a healthcare provider indicative of the reliability of the at least one sensor signal, wherein the assessing the reliability of the at least one sensor signal comprises comparing the at least one metric with at least a first predetermined threshold and a second predetermined threshold, wherein the at least one sensor signal is assessed to not be drifting or the at least one sensor is assessed to be stable, or both, if an absolute value of the underlying trend is less than the first predetermined threshold, wherein the at least one sensor signal is assessed to be drifting or the at least one sensor is assessed to be unstable, or both, if the absolute value of the underlying trend is between the first and second predetermined thresholds, wherein the at least one sensor is assessed to be dying, if the absolute value of the underlying trend is greater than the second predetermined threshold, and wherein the determining of the at least one metric assessing the underlying trend comprises determining the at least one metric using a slope of a linear regression that is derived at least partly from the monotonic curve.

3. A method comprising:

obtaining a series of samples of at least one sensor signal that is responsive to a blood glucose level of a patient wherein the at least one sensor signal is generated by a glucose sensor during a time that the glucose sensor is in contact with the patient;

determining, using the series of samples and using one or more processors, at least one metric assessing an underlying trend of a change in responsiveness of the at least one sensor signal to the blood glucose level of the patient over time;

assessing a reliability of the at least one sensor signal to respond to the blood glucose level of the patient using the at least one metric assessing the underlying trend and using the one or more processors; and in response to the assessing the reliability of the at least one sensor signal, altering an infusion treatment for the patient, or transmitting notification to the patient or a healthcare provider indicative of the reliability of the at least one sensor signal, wherein the assessing the reliability of the at least one sensor signal comprises comparing the at least one metric with at least a first predetermined threshold and a second predetermined threshold, wherein the at least one sensor signal is assessed to not be drifting or the at least one sensor is assessed to be stable, or both, if an absolute value of the underlying trend is less than the first predetermined threshold, wherein the at least one sensor signal is assessed to be drifting or the at least one sensor is assessed to be unstable, or both, if the absolute value of the underlying trend is between the first and second predetermined thresholds, wherein the at least one sensor is assessed to be dying, if the absolute value of the underlying trend is greater than the second predetermined threshold, and wherein the determining of the at least one metric assessing the underlying trend comprises determining the at least one metric by iteratively updating a trend estimation at multiple samples of the series of samples of the at least one sensor signal based at least partly on a trend estimation at a previous sample and a growth term.

4. A method comprising:

obtaining a series of samples of at least one sensor signal that is responsive to a blood glucose level of a patient wherein the at least one sensor signal is generated by a glucose sensor during a time that the glucose sensor is in contact with the patient;

determining, using the series of samples and using one or more processors, at least one metric assessing an underlying trend of a change in responsiveness of the at least one sensor signal to the blood glucose level of the patient over time;

assessing a reliability of the at least one sensor signal to respond to the blood glucose level of the patient using the at least one metric assessing the underlying trend and using the one or more processors; and in response to the assessing the reliability of the at least one sensor signal, altering an infusion treatment for the patient, or transmitting notification to the patient or a healthcare provider indicative of the reliability of the at least one sensor signal, wherein the assessing the reliability of the at least one sensor signal comprises comparing the at least one metric with at least a first predetermined threshold and a second predetermined threshold, wherein the at least one sensor signal is assessed to not be drifting or the at least one sensor is assessed to be stable, or both, if an absolute value of the underlying trend is less than the first predetermined threshold, wherein the at least one sensor signal is assessed to be drifting or the at least one sensor is assessed to be unstable, or both, if the absolute value of the underlying trend is between the first and second predetermined thresholds, wherein the at least one sensor is assessed to be dying, if the absolute value of the underlying trend is greater than the second predetermined threshold, and wherein the determining of the at least one metric assessing the underlying trend comprises determining the at least one metric by:

decomposing the at least one sensor signal as represented by the series of samples using at least one empirical mode decomposition and one or more spline functions to derive a monotonic curve; and calculating the slope of a linear regression, the linear regression being derived at least partly from the monotonic curve.

5. A method comprising:

obtaining a series of samples of at least one sensor signal that is responsive to a blood glucose level of a patient wherein the at least one sensor signal is generated by a glucose sensor during a time that the glucose sensor is in contact with the patient;

determining, using the series of samples and using one or more processors, at least one metric assessing an underlying trend of a change in responsiveness of the at least one sensor signal to the blood glucose level of the patient over time;

assessing a reliability of the at least one sensor signal to respond to the blood glucose level of the patient using the at least one metric assessing the underlying trend and using the one or more processors; and in response to the assessing the reliability of the at least one sensor signal, altering an infusion treatment for the patient, or transmitting notification to the patient or a healthcare provider indicative of the reliability of the at least one sensor signal, wherein the assessing the reliability of the at least one sensor signal comprises comparing the at least one metric with at least a first predetermined threshold and a second predetermined threshold, wherein the at least one sensor signal is assessed to not be drifting or the at least one sensor is assessed to be stable, or both, if an absolute value of the underlying trend is less than the first predetermined threshold, wherein the at least one sensor signal is assessed to be drifting or the at least one sensor is assessed to be unstable, or both, if the absolute value of the underlying trend is between the first and second predetermined thresholds, wherein the at least one sensor is assessed to be dying, if the absolute value of the underlying trend is greater than the second predetermined threshold, and wherein the determining of the at least one metric assessing the underlying trend comprises determining the at least one metric by:

decomposing the at least one sensor signal as represented by the series of samples using at least one discrete wavelet transform; and reconstructing a smoothed signal from one or more approximation coefficients resulting from the at least one discrete wavelet transform.

6. An apparatus for use with a healthcare provider and with at least one sensor configured to generate at least one sensor signal that is responsive to a blood glucose level of a patient, the apparatus comprising:

a controller to obtain a series of samples of the at least one sensor signal, the controller comprising one or more processors to:

determine, using the series of samples, at least one metric assessing an underlying trend of a change in responsiveness of the at least one sensor signal to the blood glucose level of the patient over time;

assess a reliability of the at least one sensor signal to respond to the blood glucose level of the patient using the at least one metric assessing the underlying trend, wherein the assessing of the reliability of the at least one sensor signal comprises comparing the at least one metric with at least a first predetermined threshold and a second predetermined threshold; and in response to the assessing the reliability of the at least one sensor signal, alter an infusion treatment for the patient, or transmit notification to the patient or the healthcare provider indicative of the reliability of the at least one sensor signal, wherein the one or more processors are further to assess the at least one sensor signal to not be drifting or to assess the at least one sensor to be stable, or both, if an absolute value of the underlying trend is less than the first predetermined threshold, wherein the one or more processors are further to assess the at least one sensor signal to be drifting or to assess the at least one sensor to be unstable, or both, if the absolute value of the underlying trend is between the first and second predetermined thresholds, wherein the one or more processors are further to assess the at least one sensor to be dying, if the absolute value of the underlying trend is greater than the second predetermined threshold, and wherein the one or more processors are further to determine the at least one metric assessing the underlying trend by using a slope of a linear regression that is derived at least partly from the series of samples of the at least one sensor signal.

7. An apparatus for use with a healthcare provider and with at least one sensor configured to generate at least one sensor signal that is responsive to a blood glucose level of a patient, the apparatus comprising:

a controller to obtain a series of samples of the at least one sensor signal, the controller comprising one or more processors to:

transform the series of samples of the at least one sensor signal to derive a monotonic curve;

determine, using the series of samples, at least one metric assessing an underlying trend of a change in responsiveness of the at least one sensor signal to the blood glucose level of the patient over time;

assess a reliability of the at least one sensor signal to respond to the blood glucose level of the patient using the at least one metric assessing the underlying trend, wherein the assessing of the reliability of the at least one sensor signal comprises comparing the at least one metric with at least a first predetermined threshold and a second predetermined threshold; and in response to the assessing the reliability of the at least one sensor signal, alter an infusion treatment for the patient, or transmit notification to the patient or the healthcare provider indicative of the reliability of the at least one sensor signal, wherein the one or more processors are further to assess the at least one sensor signal to not be drifting or to assess the at least one sensor to be stable, or both, if an absolute value of the underlying trend is less than the first predetermined threshold, wherein the one or more processors are further to assess the at least one sensor signal to be drifting or to assess the at least one sensor to be unstable, or both, if the absolute value of the underlying trend is between the first and second predetermined thresholds, wherein the one or more processors are further to assess the at least one sensor to be dying, if the absolute value of the underlying trend is greater than the second predetermined threshold, and wherein the one or more processors are further to determine the at least one metric assessing the underlying trend by using a slope of a linear regression that is derived at least partly from the monotonic curve.

8. An apparatus for use with a healthcare provider and with at least one sensor configured to generate at least one sensor signal that is responsive to a blood glucose level of a patient, the apparatus comprising:

a controller to obtain a series of samples of the at least one sensor signal, the controller comprising one or more processors to:

determine, using the series of samples, at least one metric assessing an underlying trend of a change in responsiveness of the at least one sensor signal to the blood glucose level of the patient over time;

assess a reliability of the at least one sensor signal to respond to the blood glucose level of the patient using the at least one metric assessing the underlying trend, wherein the assessing of the reliability of the at least one sensor signal comprises comparing the at least one metric with at least a first predetermined threshold and a second predetermined threshold; and in response to the assessing the reliability of the at least one sensor signal, alter an infusion treatment for the patient, or transmit notification to the patient or the healthcare provider indicative of the reliability of the at least one sensor signal, wherein the one or more processors are further to assess the at least one sensor signal to not be drifting or to assess the at least one sensor to be stable, or both, if an absolute value of the underlying trend is less than the first predetermined threshold, wherein the one or more processors are further to assess the at least one sensor signal to be drifting or to assess the at least one sensor to be unstable, or both, if the absolute value of the underlying trend is between the first and second predetermined thresholds, wherein the one or more processors are further to assess the at least one sensor to be dying, if the absolute value of the underlying trend is greater than the second predetermined threshold, and wherein the one or more processors are further to determine the at least one metric assessing the underlying trend by iteratively updating a trend estimation at multiple samples of the series of samples of the at least one sensor signal based at least partly on a trend estimation at a previous sample and a growth term.

9. An apparatus for use with a healthcare provider and with at least one sensor configured to generate at least one sensor signal that is responsive to a blood glucose level of a patient, the apparatus comprising:

a controller to obtain a series of samples of the at least one sensor signal, the controller comprising one or more processors to:

determine, using the series of samples, at least one metric assessing an underlying trend of a change in responsiveness of the at least one sensor signal to the blood glucose level of the patient over time;

assess a reliability of the at least one sensor signal to respond to the blood glucose level of the patient using the at least one metric assessing the underlying trend, wherein the assessing of the reliability of the at least one sensor signal comprises comparing the at least one metric with at least a first predetermined threshold and a second predetermined threshold; and in response to the assessing the reliability of the at least one sensor signal, alter an infusion treatment for the patient, or transmit notification to the patient or the healthcare provider indicative of the reliability of the at least one sensor signal, wherein the one or more processors are further to assess the at least one sensor signal to not be drifting or to assess the at least one sensor to be stable, or both, if an absolute value of the underlying trend is less than the first predetermined threshold, wherein the one or more processors are further to assess the at least one sensor signal to be drifting or to assess the at least one sensor to be unstable, or both, if the absolute value of the underlying trend is between the first and second predetermined thresholds, wherein the one or more processors are further to assess the at least one sensor to be dying, if the absolute value of the underlying trend is greater than the second predetermined threshold, and wherein the one or more processors are further to determine the at least one metric assessing the underlying trend by:

decomposing the at least one sensor signal as represented by the series of samples using at least one empirical mode decomposition and one or more spline functions to derive a monotonic curve; and calculating the slope of a linear regression, the linear regression being derived at least partly from the monotonic curve.

10. An apparatus for use with a healthcare provider and with at least one sensor configured to generate at least one sensor signal that is responsive to a blood glucose level of a patient, the apparatus comprising:

a controller to obtain a series of samples of the at least one sensor signal, the controller comprising one or more processors to:

determine, using the series of samples, at least one metric assessing an underlying trend of a change in responsiveness of the at least one sensor signal to the blood glucose level of the patient over time;

assess a reliability of the at least one sensor signal to respond to the blood glucose level of the patient using the at least one metric assessing the underlying trend, wherein the assessing of the reliability of the at least one sensor signal comprises comparing the at least one metric with at least a first predetermined threshold and a second predetermined threshold; and in response to the assessing the reliability of the at least one sensor signal, alter an infusion treatment for the patient, or transmit notification to the patient or the healthcare provider indicative of the reliability of the at least one sensor signal, wherein the one or more processors are further to assess the at least one sensor signal to not be drifting or to assess the at least one sensor to be stable, or both, if an absolute value of the underlying trend is less than the first predetermined threshold, wherein the one or more processors are further to assess the at least one sensor signal to be drifting or to assess the at least one sensor to be unstable, or both, if the absolute value of the underlying trend is between the first and second predetermined thresholds, wherein the one or more processors are further to assess the at least one sensor to be dying, if the absolute value of the underlying trend is greater than the second predetermined threshold, and wherein the one or more processors are further to determine the at least one metric assessing the underlying trend by:

decomposing the at least one sensor signal as represented by the series of samples using at least one discrete wavelet transform; and reconstructing a smoothed signal from one or more approximation coefficients resulting from the at least one discrete wavelet transform.

\* \* \* \* \*